(12) United States Patent
Morin

(10) Patent No.: US 10,837,954 B2
(45) Date of Patent: *Nov. 17, 2020

(54) NANOPORE DETECTION OF SMALL MOLECULES THROUGH COMPETITION ASSAYS

(71) Applicant: Ontera Inc., Santa Cruz, CA (US)

(72) Inventor: Trevor J. Morin, Santa Cruz, CA (US)

(73) Assignee: Ontera Inc., Santa Cruz, CA (US)

(*) Notice: Subject to any disclaimer, the term of this patent is extended or adjusted under 35 U.S.C. 154(b) by 166 days.

This patent is subject to a terminal disclaimer.

(21) Appl. No.: 15/965,168

(22) Filed: Apr. 27, 2018

(65) Prior Publication Data

US 2018/0313814 A1 Nov. 1, 2018

Related U.S. Application Data

(63) Continuation of application No. 15/501,413, filed as application No. PCT/US2016/022210 on Mar. 11, 2016, now Pat. No. 9,983,191.

(60) Provisional application No. 62/131,693, filed on Mar. 11, 2015.

(51) Int. Cl.
| | | |
|---|---|---|
| G01N 33/487 | (2006.01) | |
| C12Q 1/6816 | (2018.01) | |
| G01N 33/543 | (2006.01) | |
| C12Q 1/6825 | (2018.01) | |
| C12Q 1/6869 | (2018.01) | |

(52) U.S. Cl.
CPC ..... *G01N 33/48721* (2013.01); *C12Q 1/6816* (2013.01); *C12Q 1/6825* (2013.01); *C12Q 1/6869* (2013.01); *G01N 33/54306* (2013.01); *G01N 33/54366* (2013.01)

(58) Field of Classification Search
None
See application file for complete search history.

(56) References Cited

U.S. PATENT DOCUMENTS

| | | | |
|---|---|---|---|
| 9,983,191 B2 * | 5/2018 | Morin | C12Q 1/6869 |
| 10,048,245 B2 * | 8/2018 | Morin | G01N 33/48721 |
| 10,495,628 B2 * | 12/2019 | Morin | G01N 33/48721 |
| 10,597,702 B2 * | 3/2020 | Morin | C12Q 2563/137 |
| 2003/0022150 A1 | 1/2003 | Sampson et al. | |
| 2005/0026202 A1 | 2/2005 | Edman et al. | |
| 2009/0222215 A1 | 9/2009 | Fernandez | |
| 2010/0197515 A1 | 8/2010 | Van Harpen et al. | |

(Continued)

FOREIGN PATENT DOCUMENTS

| | | |
|---|---|---|
| JP | 2011-501806 A | 1/2011 |
| JP | 2014-173936 A | 9/2014 |

(Continued)

OTHER PUBLICATIONS

Benner, S., et al., "Sequence-Specific Detection of Individual DNA Polymerase Complexes in Real Time Using a Nanopore." Nature Nanotechnology, vol. 2, No. 11, Oct. 28, 2007, pp. 718-724.

(Continued)

*Primary Examiner* — Robert T. Crow
(74) *Attorney, Agent, or Firm* — Fenwick & West LLP

(57) ABSTRACT

Disclosed herein are methods and compositions for detection of target small molecules in a mixed sample by performing a competition assay between the target and a surrogate and subsequently detecting the complex types in a nanopore device.

24 Claims, 19 Drawing Sheets

(56) References Cited

U.S. PATENT DOCUMENTS

| | | |
|---|---|---|
| 2013/0071837 A1 | 3/2013 | Winters-Hilt et al. |
| 2013/0203610 A1 | 8/2013 | Meller et al. |
| 2013/0233709 A1 | 9/2013 | Dunbar et al. |
| 2014/0329225 A1 | 11/2014 | Morin |
| 2014/0378331 A1 | 12/2014 | Morin |
| 2018/0155768 A1 | 6/2018 | Cohen et al. |

FOREIGN PATENT DOCUMENTS

| | | |
|---|---|---|
| WO | WO 2003/044482 A2 | 5/2003 |
| WO | WO 2008/005674 A2 | 1/2008 |
| WO | WO 2013/012881 A2 | 1/2013 |
| WO | WO 2015/031399 A1 | 3/2015 |
| WO | WO 2018/093976 A1 | 5/2018 |

OTHER PUBLICATIONS

Bezrukov S. M. et al: "Counting Polymers Moving Through a Single Ion Channel", Nature, Jul. 28, 1994, pp. 279-281, vol. 370, Nature Publishing Group, United Kingdom.

Communication pursuant to Article 94(3) EPC for European Patent Application No. EP 14733761.2, dated Jan. 17, 2017, 3 Pages.

Haque, et al., "Solid-State and Biological Nanopore for Real-Time Sensing of Single Chemical and Sequencing of DNA," Nano Today, 2013, 8, pp. 56-74.

Howorka, et al., "Nanopore Analytics: Sensing of Single Molecules," Chem. Soc. Rev., 2009, 38, pp. 2360-2384.

Kasianowicz J. et al: "Simultaneous Multianalyte Detection with a Nanometer-Scale Pore", Analytical Chemistry, May 15, 2001, pp. 2268-2272, vol. 73(10).

Keyser, U. et al., "Direct Force Measurements on DNA in a Solid-State Nanopore," Nature Physics, vol. 2, Jul. 1, 2006, pp. 473-477.

Kowalczyk, S., et al., "Modeling the conductance and DNA blockade of solid-state nanopores," Nanotechnology, 2011, vol. 22, pp. 1-5.

Miles, et al., "Single Molecule Sensing With Solid-State Nanopores: Novel Materials, Methods, and Applications," Chem Soc Rev, 2013, 42(15), pp. 1-15.

Morin, T.J., et al., "Nanopore-based target sequence detection," submitted to PLOS One, Dec. 31, 2015, Published on May 5, 2016, pp. 1-21.

Niemeyer C M: "The developments of semisynthetic DNA-protein conjugates", Trends in Biotechnology, Sep. 2002, pp. 395-401, vol. 20(9), Elsevier Publications, Cambridge, GB.

Office Action for Japanese Patent Application No. JP 2017-547462, dated Mar. 19, 2018, 6 Pages.

Office Action for U.S. Appl. No. 15/160,697, dated Jan. 11, 2017, 32 Pages.

Office Action for U.S. Appl. No. 14/270,283, dated Dec. 11, 2015, 6 Pages.

Patent Cooperation Treaty, International Search Report and Written Opinion of the International Searching Authority, International Patent Application No. PCT/US2016/022210, dated Jun. 3, 2016, 15 Pages.

PCT International Preliminary Report on Patentability for PCT/US2014/036861, dated Sep. 2, 2015, 8 Pages.

PCT International Search Report and Written Opinion for International Application No. PCT/US2014/036861, dated Sep. 18, 2014, 12 pages.

PCT Written Opinion of the International Preliminary Examining Authority for PCT/US2014/036861, dated Apr. 15, 2015, 7 Pages.

PCT International Search Report and Written Opinion for PCT/US2014/046397, dated Feb. 2, 2015, 11 Pages.

Reiner, et al., "Disease Detection and Management Via Single Nanopore-Based Sensors," Chemical Reviews, 2012, 112, pp. 6431-6451.

Singer, et al., "Nanopore Based Sequence Specific Detection of Duplex DNA for Genomic Profiling," Nano Lett., 2010, 10, pp. 738-742.

Wang, H., et al., "Measuring and Modeling the Kinetics of individual DNA-DNA Polymerase Complexes on a Nanopore." ACS Nano, vol. 7, No. 5, May 28, 2013, pp. 3876-3886.

Wanunu M. et al: "DNA Profiling Using Solid-State Nanopores: Detection of DNA-Binding Molecules", Nano Letters, Oct. 14, 2009, pp. 3498-3502, vol. 9 (10).

Winters-Hilt S. "Nanopore Detector based analysis of single-molecule conformational kinetics and binding interactions", Sep. 26, 2006, pp. 1-27, vol. 7(2), BMC Bioinformatics, Biomed Central, London, GB.

United States Office Action, U.S. Appl. No. 15/501,413, dated Aug. 30, 2017, nine pages.

Extended European Search Report, European Application No. 16762680.3, dated Jun. 21, 2018, 7 pages.

* cited by examiner

NANOPORE DETECTION OF SMALL MOLECULES THROUGH COMPETITION ASSAYS

CROSS-REFERENCE TO RELATED APPLICATION

This application is a continuation of U.S. application Ser. No. 15/501,413, filed Feb. 2, 2017, now U.S. Pat. No. 9,983,191, issued May 29, 2018, which is a 35 U.S.C. 371 national stage filing of International Application No. PCT/US2016/022210, filed Mar. 11, 2016, which claims the benefit of U.S. Provisional Patent Application No. 62/131,693, filed Mar. 11, 2015, the disclosures of which are incorporated herein by reference in their entireties.

BACKGROUND

Small molecules play an important role in many biological functions. Because small molecules can alter the functions of proteins, for example, by binding to them and inhibiting or activating their normal functions, they can perturb/disrupt the systems in which the protein operates. In turn, such disruptions can trigger diseases or accelerate the progression of diseases. By controlling small molecule dosage, on the other hand, one can uncover the details about the role(s) the protein plays within these systems (Stockwell, Brent R. "Exploring biology with small organic molecules." *Nature* 432.7019 (2004): 846-854). Detecting the presence and concentration of small molecules can also be used to assess the result of a metabolic process, such as drug metabolism, which could benefit and accelerate clinical trials and drug efficacy studies. Beyond human and animal diagnostics, small molecules can also be used to assess the status of the environment, including for monitoring agricultural plant stress and water quality. The ability to detect and accurately quantitate small molecules is therefore valuable across many domains of biotechnology.

There are a number of available methods to measure small molecules; some are inexpensive, but lack accuracy and sensitivity, others are very sensitive, but costly and complex. Less expensive high throughput methods generally involve binding a dye to the target molecule of interest and detecting aggregate fluorescence or absorbance of the sample. This technique can be hampered by non-specificity of the dye or interfering molecules that create high false positives and/or high false negatives. More complex analytical methods, including high performance liquid chromatography and mass spectrometry, are able to precisely measure target small molecules, but are complex and costly and require dedicated lab space and trained personnel. What is needed, therefore, is a method of detecting small molecules that is cost effective (similar to a dye binding assays), provides high specificity, sensitivity, and accuracy, and can be performed on a portable device. A preferred analytical test for detection and/or quantification of small molecules would not be tethered to a dedicated lab and would not require specialized equipment or trained personnel. Additionally, a preferred analytical device would be of low cost and high reproducibility. Therefore, methods for providing accurate and low-cost analytical results on low cost devices that tolerate a range of nanopore geometries and/or larger nanopores are needed.

SUMMARY

Disclosed herein are competition assays for detection of small molecules using a nanopore.

Target molecules of a sufficient size (>20 kDa) when passed through a solid-state nanopore cause a change in the current impedance, translocation time, or other measurable parameter. In the event the target molecule is not sufficiently big, and thus does not cause a noticeable change, an additional molecule/reagent can be used to aid in detection. This detection reagent would bind to the small molecule or to the "capture ligand-molecule complex" (e.g. peptide detection is aided by a monoclonal antibody (mAb) that recognizes a peptide/aptamer complex).

However, there still may exists small molecules (e.g. drug compounds) for which this strategy is not ideal. For example, it may be difficult to create a detection reagent to the target small molecule once it's capture due to the reduction of available surface area for binding additional detection molecules. Therefore, we have devised a new strategy that enables both detection of the small molecule compounds, and the ability to measure binding affinities and kinetics ($K_{on}$, $K_{off}$, $K_d$, $K_m$, etc.). The method is also applicable to investigating complex assembly (for example, HIV Env protein monomer, dimer, or trimers).

In some embodiments, provided herein is a method for detecting the presence or absence of a target molecule suspected to be present in a sample, the method comprising: providing a device comprising a layer, wherein said layer separates an interior space of the device into a first volume and a second volume, wherein said layer comprises a nanopore connecting said first volume and said second volume, and wherein the device comprises a sensor configured to identify objects passing through the nanopore; providing a surrogate molecule, a fusion molecule, and a polymer scaffold, said fusion molecule comprising a polymer scaffold binding domain adapted to bind said polymer scaffold to form a scaffold/fusion molecule complex, and said fusion molecule comprising a target molecule binding domain adapted to bind said surrogate molecule or said target molecule; performing a competition assay by combining said surrogate molecule and said fusion molecule with said sample, wherein said target molecule competes with said surrogate molecule for binding to said target molecule binding domain if said target molecule is present in said sample; loading said sample into said first volume; applying a voltage across said nanopore, wherein said first volume comprises said polymer scaffold, said fusion molecule, said surrogate molecule, and said sample suspected of comprising said target molecule, wherein said polymer scaffold is hybridized to said fusion molecule, and wherein said fusion molecule is hybridized to said surrogate molecule or said target molecule.

In some embodiments, the applied voltage induces translocation of said scaffold/fusion molecule complex bound to said target molecule or said surrogate molecule from said first volume through said nanopore to generate changes in electrical signal detected by said sensor. In some embodiments, the method further comprises recording the detected changes in electrical signal as a function of time. In a further embodiment, the method comprises analyzing the detected and recorded changes in electrical signal as a function of time to determine the presence or absence of said target small molecule in said sample.

In some embodiments, the competition assay is performed after loading said sample into said first volume. In some embodiments, the competition assay is performed before loading said sample into said first volume.

In some embodiments, the surrogate molecule comprises maleimide polyethylene glycol. In some embodiments, the surrogate molecule comprises a chemically reactive group selected from the group consisting of: a ketone, an aldehyde, an isocyanate, an amine, a carboxylic acid, a halide, an ester, a maleimide, a thiol, a dicyclocarbimide, a pyridyl, a pyridyl disulfide, and an acetyl. In some embodiments, the surrogate molecule comprises a strong or weak nucleophile or electrophile. In some embodiments, the surrogate molecule comprises a peptide, dendrimer, nucleic acid, nano or micro bead or particle, quantum dot, protein, polynucleotide, liposome, antibody, or antibody fragment. In some embodiments, the surrogate molecule comprises a payload binding site adapted to bind to a payload molecule. In a further embodiment, the payload molecule is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid. In some embodiments, the payload molecule comprises an electrical charge. In some embodiments, the charged payload molecule is selected form the group consisting of: a peptide, an amino acid, a charged nanoparticle, a synthetic molecule, a nucleotide, a polynucleotide, a metal, or an ion. In some embodiments, the surrogate molecule is bound to said payload molecule via an interaction selected from the group consisting of: a covalent bond, a hydrogen bond, an ionic bond, a van der Waals force, a hydrophobic interaction, a cation-pi interaction, a planar stacking interaction, a metallic bond, and a biotin-avidin interaction.

In some embodiments, the target molecule comprises a small molecule less than 30,000 Da, 20,000 Da, 10,000 Da, 5,000 Da, 2,000 Da, 1,000 Da, 500 Da, 200 Da, 100 Da, 50 Da, 20 Da, or 10 Da in size. In some embodiments, the target molecule comprises a peptide, insulin, oxytocin, an amino acid, a protein or domain of a protein, nucleotide, oligomers, DNA, RNA, PNA, LNA, BNA, hormones, lipids, cholesterols, metabolites, sugars, glycans, peptidoglycan, polyglycan, phospholipids, steroids, chemically synthesized agonist and antagonists, synthesized derivatives of a polynucleic acid, polycyclic aromatic hydrocarbons, carbon breakdown byproducts, dioxin, cyclohexamide, vitamins, adenosine triphosphate and ATP analogs, neurotransmitters, dopamine, L-dopa, serotonin, metals, electrolytes, organometals, narcotics and narcotic derivatives, hyaluronic acid, or retinol.

In some embodiments, the fusion molecule comprises a peptide nucleic acid. In some embodiments, the fusion molecule comprises a cysteine-tagged bis peptide nucleic acid. In some embodiments, the fusion molecule comprises a bridged nucleic acid, locked nucleic acid, biotin, streptavidin, a streptavidin derivative, zinc finger protein, zfp binding domain, CRISPR domain, TALEN, DNA, PNA, or RNA oligomer.

In some embodiments, the polymer scaffold comprises a negatively or positively charged polymer adapted to translocate through said nanopore from said first volume to said second volume upon application of a voltage potential to said nanopore. In some embodiments, the polymer scaffold comprises a molecule selected from the group consisting of: deoxyribonucleic acid (DNA), ribonucleic acid (RNA), peptide nucleic acid (PNA), DNA/RNA hybrid, and polypeptide.

In some embodiments, the sensor is configured to identify objects passing through only a single nanopore. In some embodiments, the sensor is an electrical sensor. In some embodiments, the sensor detects current flow through said nanopore upon application of a voltage across said nanopore.

In some embodiments, the analysis of changes in electrical signal as a function of time comprises segregating events due to translocation of said scaffold/fusion complex bound to said surrogate molecule through the nanopore and events due to translocation of said scaffold/fusion complex bound to said target molecule through said nanopore. In some embodiments, the method of target small molecule detection provided herein provides a confidence of detection of said target small molecules of greater than 90%, 95%, 98%, or 99%. In some embodiments, the sample is not purified prior to loading into said first volume.

In some embodiments, the nanopore is at least 5 nm, 10 nm, 20 nm, 30 nm, 40 nm, or 50 nm in diameter. In some embodiments, the device comprises at least two nanopores in series, and wherein said amplicon bound to said payload molecule is simultaneously in said at least two nanopores during translocation.

Also provided herein is a kit comprising a device comprising a nanopore, wherein said device comprises a layer separating an interior space of the device into a first volume and a second volume, wherein said layer comprises a nanopore through said layer connecting said first volume and said second volume, and wherein the device comprises a sensor configured to identify objects passing through the nanopore; a surrogate molecule, a fusion molecule, and a polymer scaffold, said fusion molecule comprising a polymer scaffold binding domain adapted to bind said polymer scaffold to form a scaffold/fusion molecule complex, and said fusion molecule comprising a target molecule binding domain adapted to bind said surrogate molecule or said target molecule; and instructions for use to detect the presence or absence of said target small molecule via observing the results of a competition assay in said device.

In some embodiments, the surrogate molecule of the kit comprises maleimide polyethylene glycol. In some embodiments, the surrogate molecule of the kit comprises a chemically reactive group selected from the group consisting of: a ketone, an aldehyde, an isocyanate, an amine, a carboxylic acid, a halide, an ester, a maleimide, a thiol, a dicyclocarbimide, a pyridyl, a pyridyl disulfide, and an acetyl. In some embodiments, the surrogate molecule of the kit comprises a weak or strong nucleophile or electrophile. In some embodiments, the surrogate molecule of the kit comprises a peptide, dendrimer, nucleic acid, nano or micro bead or particle, quantum dot, protein, polynucleotide, liposome, or antibody. In some embodiments, the surrogate molecule of the kit comprises a payload binding site adapted to bind to a payload molecule.

In some embodiments, the payload molecule of the kit is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid. In some embodiments, the payload molecule of the kit comprises an electrical charge. In some embodiments, the charged payload molecule of the kit is selected form the group consisting of: a peptide, an amino acid, a charged nanoparticle, a synthetic molecule, a nucleotide, a polynucleotide, a metal, or an ion. In some embodiments, the surrogate molecule of the kit is bound to said payload molecule via an interaction selected from the group consisting of: a covalent bond, a hydrogen bond, an ionic bond, a van der Waals force, a hydrophobic interaction, a cation-pi interaction, a planar stacking interaction, a metallic bond, and a biotin-avidin interaction.

In some embodiments, the target molecule comprises a small molecule less than 30,000 Da, 20,000 Da, 10,000 Da, 5,000 Da, 2,000 Da, 1,000 Da, 500 Da, 200 Da, 100 Da, 50 Da, 20 Da, or 10 Da in size. In some embodiments, the target molecule of the kit comprises a molecule selected from the group consisting of: N-ethyl maleimide, a peptide, insulin, oxytocin, an amino acid, a protein or domain of a protein, nucleotide, oligomers, DNA, RNA, hormones, lipids, cholesterols, metabolites, sugars, glycans, peptidoglycan, polyglycan, phospholipids, steroids, chemically synthesized agonist and antagonists, synthesized derivatives (PNA, LNA, BNA), polycyclic aromatic hydrocarbons (PAH), carbon breakdown byproducts, dioxin, cyclohexamide, vitamins, adenosine triphosphate and ATP analogs, neurotransmitters, dopamine, L-dopa, serotonin, metals, electrolytes, organometals, narcotics and narcotic derivatives, hyaluronic acid, and retinol In some embodiments, the fusion molecule of the kit comprises a peptide nucleic acid. In some embodiments, the fusion molecule of the kit comprises a cysteine-tagged bis peptide nucleic acid. In some embodiments, the fusion molecule of the kit comprises a bridged nucleic acid, locked nucleic acid, biotin, streptavidin (or streptavidin derivative), zinc finger protein or zfp binding domain, CRISPR domain, TALEN, DNA or RNA oligomer, fused to a domain that binds target small molecules.

In some embodiments, the polymer scaffold of the kit comprises a negatively or positively charged polymer adapted to translocate through said nanopore from said first volume to said second volume upon application of a voltage potential to said nanopore. In some embodiments, the polymer scaffold of the kit comprises a molecule selected from the group consisting of: deoxyribonucleic acid (DNA), ribonucleic acid (RNA), peptide nucleic acid (PNA), DNA/RNA hybrid, and polypeptide.

In some embodiments, the sensor of the device in the kit is configured to identify objects passing through only a single nanopore. In some embodiments, the sensor of the device in the kit is an electrical sensor. In some embodiments, the sensor of the device in the kit detects current flow through said nanopore upon application of a voltage across said nanopore.

Also provided herein is a method for quantifying the amount of target small molecule present in a sample, the method comprising: providing a device comprising a layer, wherein said layer separates an interior space of the device into a first volume and a second volume, wherein said layer comprises a nanopore connecting said first volume and said second volume, and wherein the device comprises a sensor configured to identify objects passing through the nanopore; providing a surrogate molecule, a fusion molecule, and a polymer scaffold, said fusion molecule comprising a polymer scaffold binding domain adapted to bind said polymer scaffold to form a scaffold/fusion molecule complex, and said fusion molecule comprising a target molecule binding domain adapted to bind said surrogate molecule or said target molecule; performing a competition assay by combining said surrogate molecule and said fusion molecule with said sample, wherein said target molecule competes with said surrogate molecule for binding to said target molecule binding domain if said target molecule is present in said sample; loading said sample into said first volume; applying a voltage across said nanopore, wherein said first volume comprises said polymer scaffold, said fusion molecule, said surrogate molecule, and said sample suspected of comprising said target molecule, wherein said polymer scaffold is hybridized to said fusion molecule, and wherein said fusion molecule is hybridized to said surrogate molecule or said target molecule; comparing the capture rate of said scaffold/fusion molecules bound to said target small molecule in the nanopore with the capture rate of said scaffold/fusion molecules bound to said surrogate molecule in the nanopore to quantify the amount of target small molecule in said experimental sample.

In some embodiments of method for quantifying the amount of target small molecule present in a sample, the voltage induces translocation of said scaffold/fusion molecule complex bound to said target molecule or said surrogate molecule from said first volume through said nanopore to generate changes in electrical signal detected by said sensor. In some embodiments, the method for quantifying the amount of target small molecule present in a sample further comprises recording said changes in electrical signal as a function of time. In some embodiments, the method for quantifying the amount of target small molecule present in a sample further comprises analyzing said changes in electrical signal as a function of time to determine the presence or absence of said target small molecule in said sample.

In some embodiments of method for quantifying the amount of target small molecule present in a sample, the competition assay is performed after loading said sample into said first volume. In some embodiments of method for quantifying the amount of target small molecule present in a sample, the competition assay is performed before loading said sample into said first volume.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention. Provided also as embodiments of this disclosure are data figures that illustrate features by exemplification only, and not limitation.

DETAILED DESCRIPTION

Figure 1:
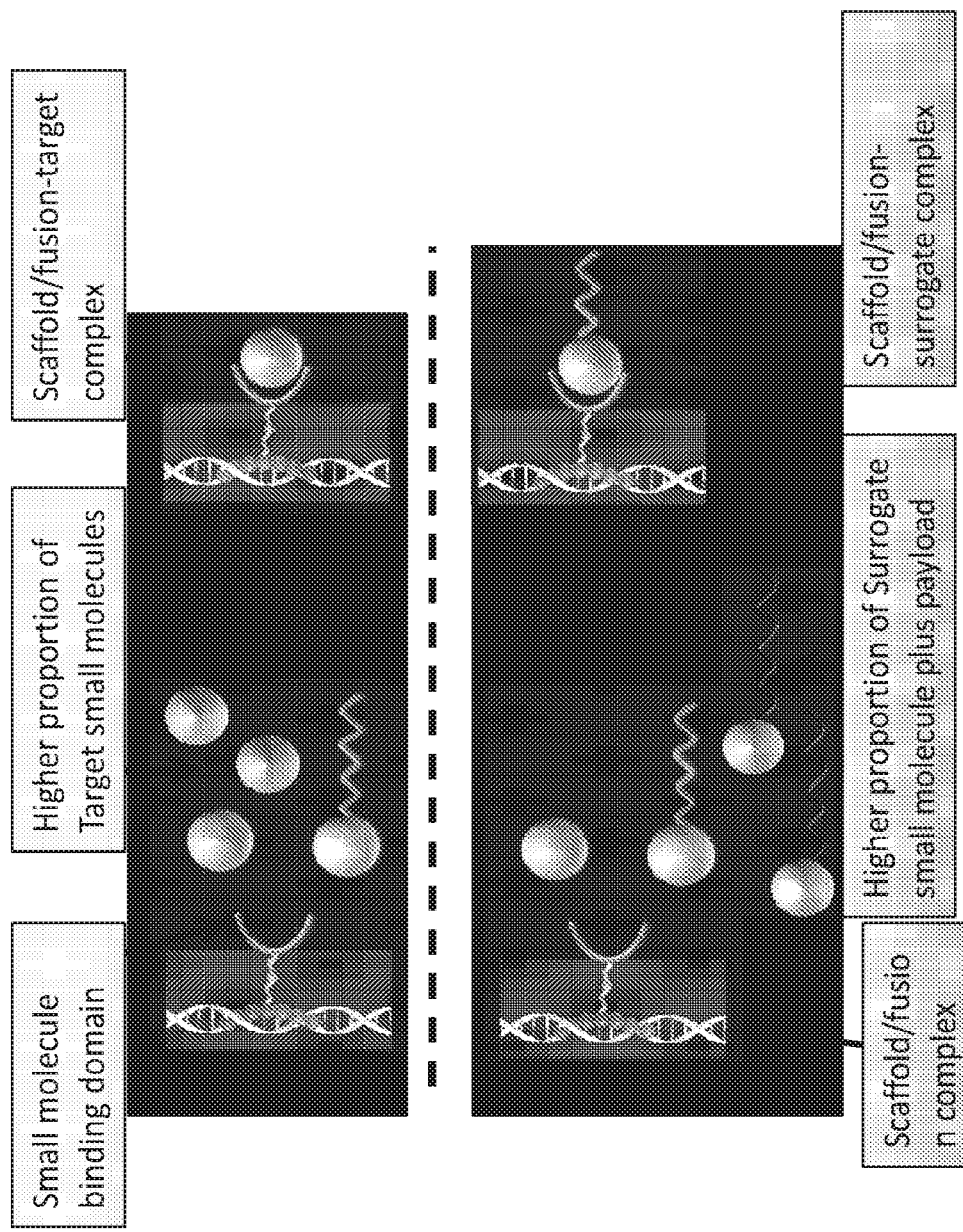
FIG. 1 depicts a schematic of the competition assay, wherein target small molecules compete with surrogate small molecules with payloads attached to bind to the small molecule binding domain of the scaffold/fusion complex.
Figure 2:
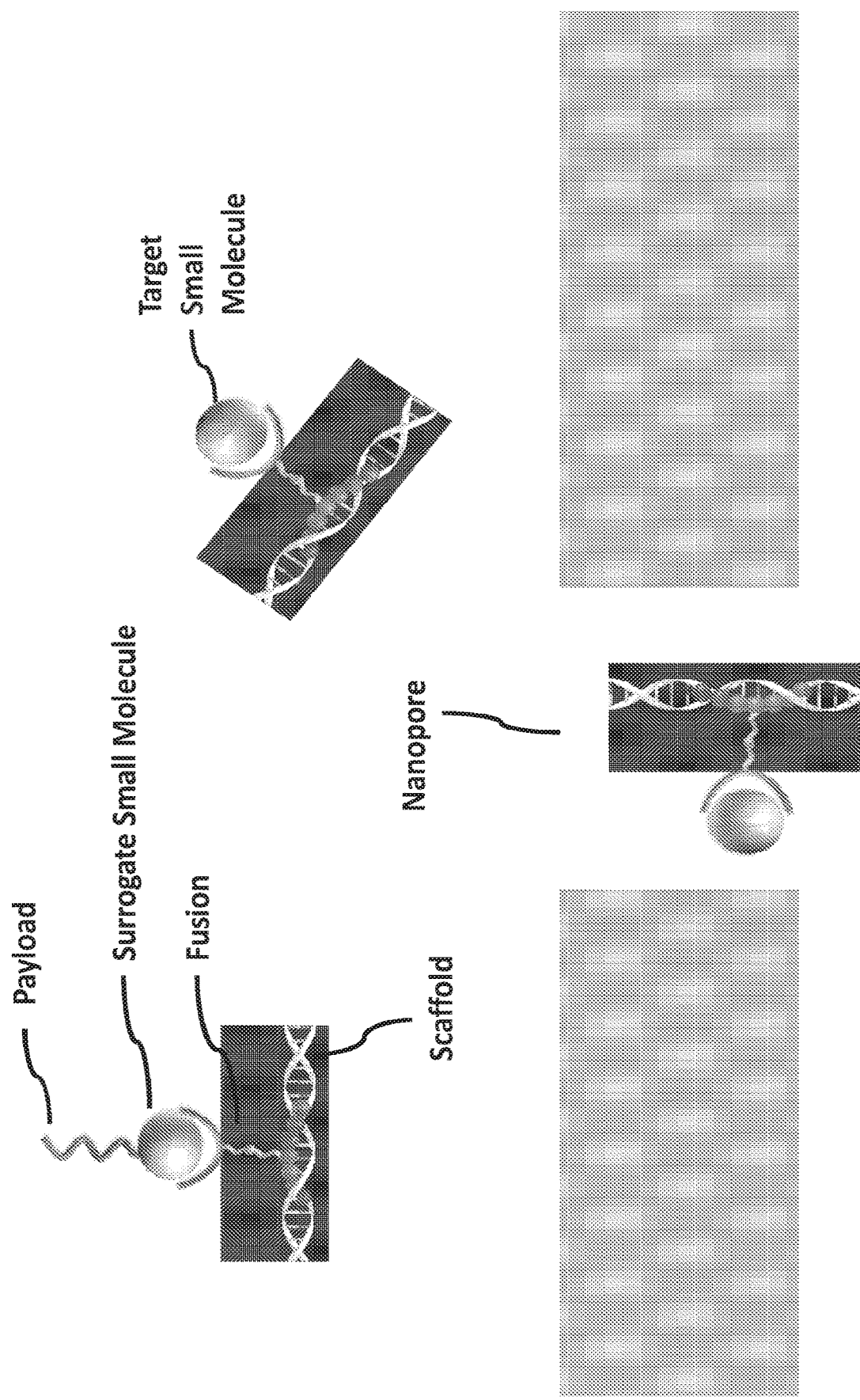
FIG. 2 depicts scaffold/fusion-target and scaffold/fusion-surrogate molecule types above and being captured into a nanopore, one at a time.
Figure 3:
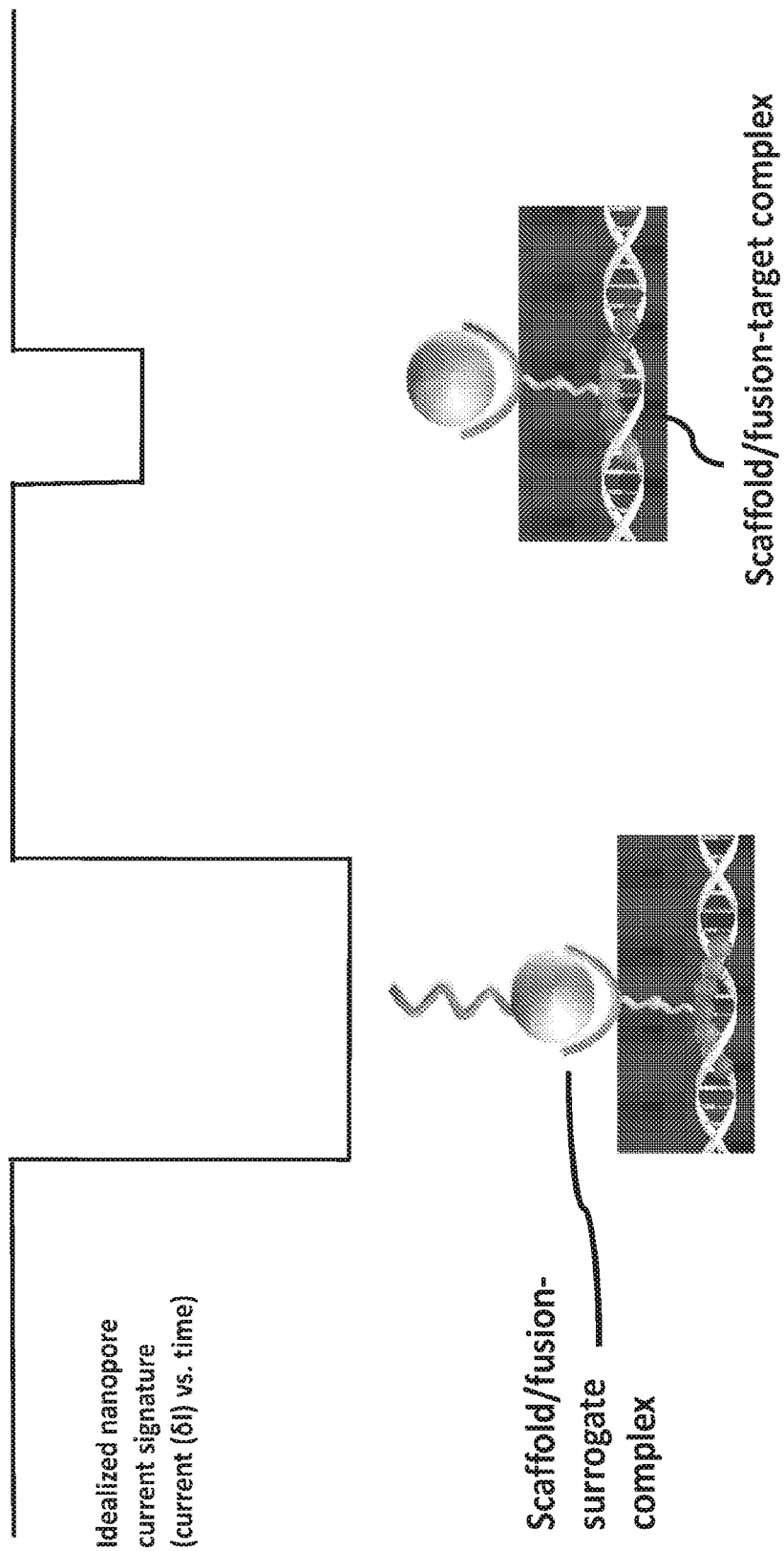
FIG. 3 depicts the idealized nanopore current event signature for the scaffold/fusion-target and the scaffold/fusion-surrogate molecule types.

Throughout this application, the text refers to various embodiments of the present devices, compositions, systems, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure in their entireties As used herein, the term "comprising" is intended to mean that the systems, devices, and methods include the recited components or steps, but not excluding others. "Consisting essentially of" when used to define systems, devices, and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary, and that equivalents of such are known in the art.

As used herein, "a device comprising a nanopore that separates an interior space" shall refer to a device having a pore that comprises an opening within a structure, the structure separating an interior space into two volumes or chambers. The device can also have more than one nanopore, and with one common chamber between every pair of pores.

As used herein, the term "fusion molecule" refers to a molecule that contains at least two domains, one that binds to a scaffold, and another that binds or reacts with a small molecule.

As used herein, the term "target small molecule" refers to the small molecule of interest that may or may not be present within a sample. In molecular biology and pharmacology, a small molecule is a low molecular weight (<1000 daltons) organic compound that helps regulate a biological process or is the breakdown product (metabolite) of a larger molecule, either man-made (i.e. synthesized drug) or product of nature (e.g. protein). In the context of this patent application, our definition of small molecule is broader, since we define it as any molecule that is too small to, by itself, to reliably create a discriminatory electrical signal when shuttled through a solid-state nanopore. In some embodiments, a small molecule can be, but is not limited to, any target molecule less than 10,000 Da in size. However, small molecules larger than 10,000 Da in size may also be difficult to detect in a nanopore, so that the competition assay described herein can be used to detect these small molecules as well.

As used herein, the term "surrogate molecule" or "surrogate small molecule" refers to a molecule, which may or may not be the same as the target small molecule. The surrogate molecule competes with the target small molecule for the same binding site or reactive site of the fusion molecule. In some embodiments, the surrogate molecule is large enough to be detected in a nanopore. In some embodiments, the surrogate molecule is a small molecule that is capable of binding to or is bound to a payload molecule. In this embodiment, the payload molecule facilitates detection of the surrogate small molecule in the nanopore. In some embodiments, the surrogate small molecule is adapted to or configured to bind to the payload molecule. Where the specification refers to a surrogate small molecule attached to a payload molecule, a small molecule without a payload may instead be used if capable of being detected in the nanopore when bound to the scaffold/fusion molecule complex.

As used herein, the term "payload" or "payload molecule" refers to molecules or compounds that are bound to the surrogate small molecule to enhance selectivity and/or sensitivity of detection of the competing small molecule in a nanopore. In some embodiments, the payload molecule is bound to the surrogate small molecule at a 1:1 ratio.

As used herein, the term "scaffold" or "polymer scaffold" refers to a negatively or positively charged polymer that translocates through a nanopore upon application of voltage. In some embodiments, a polymer scaffold capable of binding or bound to a fusion molecule. In some aspects, the polymer scaffold comprises a deoxyribonucleic acid (DNA), a ribonucleic acid (RNA), a peptide nucleic acid (PNA), a DNA/RNA hybrid, or a polypeptide. The scaffold may also be a chemically synthesized polymer, and not a naturally occurring or biological molecule. In a preferred embodiment, the polymer scaffold is dsDNA to allow more predictable signals upon translocation through the nanopore and reduce secondary structure present in ssDNA or RNA. In some embodiments, the polymer scaffold comprises a fusion molecule binding site that may reside on the end of the scaffold, or at both ends of the scaffold. The scaffold and fusion molecule may be connected via a covalent bond, a non-covalent bond, a hydrogen bond, an ionic bond, a van der Waals force, a hydrophobic interaction, a cation-pi interaction, a planar stacking interaction, or a metallic bond.

As used herein, the term "fusion" or "fusion molecule" refers to a macromolecule or compound that has two domains: 1) a scaffold-binding domain, and 2) a small molecule-binding domain or reactive site. An example fusion molecule is a PNA (for binding a dsDNA scaffold) with an aptamer attached that is specific for the small molecule of interest. A second fusion example is a PNA binding domain fused to a chemical group for selective reactivity with a specific chemical group in the small molecule of interest. The small-molecule binding domain or reactive chemical group is competent to bind the target small molecule of interest with high specificity and known or measurable affinity, and also to bind the surrogate small molecule with the payload attached.

As used herein, the term "bind" or "binding" refers to the formation of a chemical bond, e.g., a covalent bond, an ionic bond, or a metallic bond. Binding can include a stable association between two molecules via a van der Waals force, a hydrophobic interaction, a cation-pi interaction, and/or a planar stacking interaction. Binding can include bond formation between two (or more) chemically reactive groups, such as a ketone and a nucleophile, using traditional chemical or biochemical coupling techniques (with or without a catalyst). In some embodiments, the stable association between two molecules can be disrupted by competitive binding of another molecule that forms a stable interaction with the binding site.

As used herein, the term "binding site" or "binding domain" refers to a region on a molecule or compound that specifically binds to another molecule. In some embodiments, disclosed herein is a fusion molecule comprising a binding domain specific for a polymer scaffold, and further comprising a binding domain specific for a target small molecule and a surrogate molecule. The stable association (e.g., docking) between the fusion molecule and other molecules at the binding domain can be formed by non-covalent intermolecular bonding, such as ionic bonds, hydrogen bonds, and Van der Waals forces, or by covalent bonding (i.e. through chemical or biochemical reactivity) between the binding domain and the target molecule or ligand.

As used herein, the term "competition" or "competition assay" refers to the competition between the surrogate molecule (e.g., a surrogate small molecule with payload attached) and the target small molecule, both molecule types attempting to bind the target molecule binding domain on each scaffold/fusion molecule. The competition for binding to the target molecule binding domain can be competitive, non-competitive, or uncompetitive.

As used herein, the term "scaffold/fusion-target" or "scaffold/fusion-target complex" refers to the target small molecule bound to the target molecule binding domain on a scaffold/fusion molecule complex.

As used herein, the term "scaffold/fusion-surrogate" or "scaffold/fusion-surrogate complex" refers to the surrogate molecule (e.g., a payload-bound surrogate small molecule) bound to the target molecule binding domain on a scaffold/fusion molecule.

As used herein, the term "nanopore" refers to an opening (hole or channel) of sufficient size to allow the passage of particularly sized polymers. With an amplifier, voltage is applied to drive charged polymers through the nanopore, and the current through the pore detects if molecules are passing through it.

As used herein, the term "sensor" refers to a device that collects a signal from a nanopore device. In many embodiments, the sensor includes a pair of electrodes placed at two sides of a pore to measure an ionic current across the pore when a molecule or other entity, in particular a polymer scaffold, moves through the pore. In addition to the electrodes, an additional sensor, e.g., an optical sensor, may be to detect an optical signal in the nanopore device. Other sensors may be used to detect such properties as current blockade, electron tunneling current, charge-induced field effect, nanopore transit time, optical signal, light scattering, and plasmon resonance.

As used herein, the term "current measurement" refers to a series of measurements of current flow at an applied voltage through the nanopore over time. The current is expressed as a measurement to quantitate events, and the current normalized by voltage (conductance) is also used to quantitate events.

As used herein, the term "open channel" refers to the baseline level of current through a nanopore channel within a noise range where the current does not deviate from a threshold of value defined by the analysis software.

As used herein, the term "event" refers to a set of current impedance measurements that begins when the current measurement deviates from the open channel value by a defined threshold, and ends when the current returns to within a threshold of the open channel value.

As used herein, the term "current impedance signature" refers to a collection of current measurements and/or patterns identified within a detected event. Multiple signatures may also exist within an event to enhance discrimination between molecule types.

As used herein, the term "target detection event" refers to a distinctive event or current impedance signature that signals that a scaffold/fusion-target complex went through the nanopore. As used herein, the term "surrogate detection event" refers to a distinctive event or current impedance signature that signals that a scaffold/fusion-surrogate complex went through the nanopore.

A surrogate target detection event can be due to a payload that adds bulk. The added bulk of the payload molecule bound to the surrogate small molecule is what enables discrimination between a scaffold/fusion-target complex and a scaffold/fusion-surrogate complex, where discrimination is based on one or more differences in the current impedance signature.

A surrogate target detection event can be due to a payload charge. The added charge of the payload molecule bound to the surrogate small molecule is what enables discrimination between a scaffold/fusion-target complex and a scaffold/fusion-surrogate complex, where discrimination is based on one or more differences in the current impedance signature.

Aside from bulk and length, a surrogate target detection event can be due to a payload with other characteristics that enables discrimination between a scaffold/fusion-target complex and a scaffold/fusion-surrogate complex, where discrimination is based on one or more differences in the current impedance signature. Example characteristics include payload hydrophilicity, hydrophobicity, length, amino acid composition, base composition, or other chemical characteristic.

As used herein, the term "capture rate" refers to the number of events detected over time in a nanopore device. In some embodiments, the capture rate can refer specifically to the rate of capture and/or translocation of events associated with a specific complex. As described herein, the capture rate can be used to infer concentration as compared to a control with a similar mass/charge ratio under similar nanopore conditions.

Competition Assay

Disclosed herein are methods and compositions for detecting target small molecules by using a competition assay between the target and a surrogate, and using a nanopore device for discrimination between target-bound and surrogate-bound macromolecules adapted to allow detection (e.g., by current impedance signature) in a nanopore. In some embodiments, the methods, compositions, and devices disclosed herein are adapted to allow purely electrical counting of scaffold DNA-bound molecules as they pass through a nanopore. Examples provided within demonstrate "target-bound scaffold/fusion" provides a definitive and robust signal that can be discriminated from "surrogate-bound scaffold/fusion" each time a single scaffold/fusion macromolecule passes through the nanopore. This allows a fast and simple means of accurate and precise target molecule detection and quantitation from a mixed sample, allowing 100s to 1000s or more of target molecules to be individually counted and distinguished from background non-target molecules in minutes using an electrical detection method that does not require chemical or optical detection. Additionally, given the inexpensive hardware of the device, low power requirements, small size, and the tolerance to a range of nanopore geometries, fabrication and device costs are extremely low.

In some embodiments, provided herein is a method of performing a competitive binding assay to be analyzed in a nanopore device. In one embodiment, the competitive binding assay is performed using a saturation (equilibrium) analysis, where the surrogate small molecule is at a sufficient concentration to generate a saturation curve from which a $B_{max}$ value can be obtained. In some embodiments, a fixed amount of scaffold-fusion is incubated with increasing concentrations of surrogate small molecule and allowed to reach equilibrium. Then, the scaffold is passed through the pore and amount of scaffold bound by small molecule surrogate is recorded. By comparing the amount of surrogate molecule-bound scaffold/fusion complex against the concentration of surrogate molecule, a logarithmic concentration-based response curve is generated from which the maximum complex-bound ($B_{max}$) concentration of surrogate small molecule can be determined. This $B_{max}$ concentration can then used in a follow up competition assay. The $K_D$ of the binding interaction between the surrogate molecule and the fusion molecule can be calculated from a Scatchard plot where the intercept on the X-axis is equal to the $B_{max}$, the Y-axis is surrogate bound scaffold divided by unbound scaffold. For this plot, the slope is equal to the $-1/K_D$. This $K_D$ value, a concentration of surrogate small molecule that results in 50% bound scaffold, is used when generating the standard curve described below. With the $B_{max}$ calculated, a competition assay can be performed by diluting a test sample containing target small molecule to a plurality of different concentrations, incubating each concentration with the scaffold-fusion complex, and allowing the mixture to reach equilibrium. Then, the $B_{max}$ concentration of surrogate molecule is added to the mix and incubated long enough for the reaction to again reach equilibrium (e.g., typically 5-10 minutes). The reactions are placed into a nanopore device, and a voltage is applied across the nanopore to induce translocation of polymer scaffold-fusion complexes through the nanopore and to observe the electrical signature of each to determine whether the complex is bound to a surrogate molecule or to a target molecule.

In some embodiments, the capture rate of surrogate bound complexes is recorded. This capture rate can then be mapped to a standard curve that is generated by measuring capture rate of bound event (per second) (Y-axis) to concentration of surrogate bound scaffold (X-axis) to estimate the concentration of surrogate bound scaffolds in the test sample. Since the number of scaffold molecules per incubation are known, and each scaffold can only bind one small molecule, the number of small molecules can be determined. For example, if the rate of the surrogate bound scaffolds in the unknown sample matches the 50% bound rate on the standard curve, and 1 million scaffolds per ml were used in the reaction, we'd infer the small molecule concentration is 0.5 million per ml.

Assigning Statistical Significance to Detection

In some embodiments, aggregating the set of sensor measurements recorded over time and applying mathematical tools are performed to assign a numerical confidence value to detection of the target small molecule suspected to be present in a sample, as detailed in the previous section.

A quantitative method of discriminating a molecule type from background (i.e., other molecule types) based on differences in nanopore event population characteristics was recently developed (Morin, T. J., et al., "Nanopore-based target sequence detection," submitted to *PLOS One*, Dec. 31, 2015). This method of discrimination means a specific molecule type can be detected among the presence of varying types of other molecules, and that the statistical significance of detection can be assigned (e.g., detection of reagent X with 99% confidence). To apply the method to the examples provided below, we first summarize the method here.

In general terms, there are two categories of molecules in the chamber above the pore: type 1 are the scaffold/fusion-surrogate molecules, and type 2 are the scaffold/fusion-target molecules. Based on data from experiments, we identify an event signature criterion that is present in a significant fraction of type 2 events, and present in a relatively smaller fraction of type 1 events. The signature criterion could depend on δG, duration, the number and characteristics of levels within each event, and/or any other numeric value or combination of values computed from the event signal.

Note that the event signature criterion can be chosen manually, or by table look-up, or in an automated fashion. For example, prior experiments can establish the performance of positive and negative controls for a range of pore sizes and other conditions expected to be present in a given test, and the chosen criteria identified from such controls can be used (in a table look-up fashion) when comparable conditions are encountered for a given test (i.e., for a given surrogate small molecule/payload type). Automated criteria can be identified in real-time also, based on a control run just prior to a sample, for example. For detection of target small molecules from a sample in real-time, as disclosed in this application, automated criteria selection is a suitable and preferred approach. Specifically, prior to testing the sample, a control generating a type 1 event population can be used to automate the calculation of a "type 2 event boundary" that establishes the criteria for flagging "type 2-positive" events vs. "type 1-positive" events. The boundary could be computed by any method of fitting a curve around points in a 2D plot (e.g., the points being the events within the mean shift vs. duration plot). Curve fitting methods can involve least-squares, linear or quadratic programming, or any form of numerical optimization, and parameterizing the boundary via the coefficients of piece-wise polynomials or splines. Computing the convex hull can provide a boundary. Higher dimensional boundary fitting routines are also possible, e.g., using 3 properties that characterize the events (3D boundary). The resulting boundary could be polygonal, or smooth. A relevant technique, for the purpose of enclosing a subset of the events with a boundary that includes a specific percentage of the events (i.e., as a mechanism to trim outliers when enclosing the points for automated criteria identification), is to compute a z-quantile boundary, defined as the boundary of the smallest region that contains z fraction of total probability. For example, the 95%-quantile boundary is the boundary of the smallest region that contains 95% of total probability (95% of the data). Although the probability density is unknown, it can be estimated using the data and with standard numerical techniques.

Once a criterion is chosen (manually, by table look up, or in an automated fashion), an event is "tagged" as being type 2 if the signature criterion is met for that event. We define p as the probability that a capture event is type 2. In control experiments without type 2 molecules we know p=0, and in experiments that test for type 2 molecules we want to know if p>0. We define the false positive probability q1=Pr (tagged|type 1 event). In a control experiment or set of experiments with only scaffold/fusion-surrogate molecules, q1 is determined with good accuracy from a reasonable number of capture events. In a detection experiment to determine if type 2 molecules are present in bulk solution, the probability that a capture event is tagged is a function of p and can be approximated as:

$$Q(p) = (\text{Number of tagged events})/N$$

In the formula, N is the total number of events. The 99% confidence interval $Q(p) \pm Q_{sd}(p)$ can be computed with $Q_{sd}(p) = 2.57 * \text{sqrt}\{Q(p)*(1-Q(p))/N\}$, with sqrt{ } the square root function. During the course of an experiment, the value for $Q(p)$ converges and the uncertainty bounds attenuate as the number of events N increases. A plot of $Q(p) \pm Q_{sd}(p)$ as a function of recording time shows how it evolves for each reagent type (FIGS. 10, 13, 17, 19). In a control experiment without type 2 molecules, observe that $Q(0) = q1$.

In a detection experiment, type 2 molecules are present with 99% confidence when the following criteria is true:

$$Q(p) - Q_{sd}(p) > q1 \quad (1.)$$

If the criteria above is true, we conclude p>0; if it is untrue, we cannot say p>0. The framework is utilized in the Examples provided below.

Estimating the Concentration from Measured Capture Rates

In some embodiments, aggregating the set of sensor measurements recorded over time and applying mathematical tools are performed to estimate the concentration of the target small molecule suspected to be present in a sample.

In some embodiments, the process (incubate sample with scaffold/fusion reagent and perform nanopore experiments) can be repeated while varying concentration of one or more of the scaffold, fusion, surrogate small molecule and/or target small molecule suspected to be present in a sample. The data sets can then be combined to glean more information. In one embodiment, the total concentration of the target small molecule is to be estimated by applying mathematical tools to the aggregated data sets.

Following methods in the literature (Wang, Hongyun, et al., "Measuring and Modeling the Kinetics of Individual DNA-DNA Polymerase Complexes on a Nanopore." *ACS Nano* 7, no. 5 (May 28, 2013): 3876-86. doi:10.1021/nn401180j; Benner, Seico, et al., "Sequence-Specific Detection of Individual DNA Polymerase Complexes in Real Time Using a Nanopore." *Nature Nanotechnology* 2, no. 11 (Oct. 28, 2007): 718-24 (doi:10.1038/nnano.2007.344), one can apply biophysical models to nanopore data to quantitate the binding and equilibrium kinetics between the target small molecule and its substrate, and with competition between the target and the surrogate small molecules. The study in Wang et al., cited above, examined two mutually exclusive and competing binding states of a protein for its DNA substrate. The same modeling framework can be applied, but with two different molecules creating the two distinct binding configurations that can occur with each substrate molecule.

In our assays, the nanopore is sampling and measuring individual molecules from the bulk-phase. In the presence of a target molecule, every scaffold/fusion will have a target bound or a surrogate bound, and the fraction of scaffold/fusion-target complexes will be proportional to the concentration of the target. At high target concentrations relative to the surrogate concentration, binding of the target will proceed rapidly, and all of the scaffold/fusion complexes will be target bound. At lower concentrations relative to the surrogate concentration, binding of the surrogate will proceed relatively rapidly, and all of the scaffold/fusion complexes will be surrogate bound. At intermediate concentrations, a non-zero percentage of scaffold/fusion events will be flagged as being target bound (type 2), and this percentage will remain constant over time with the reaction reaching equilibrium fast in the bulk phase chamber adjacent to the nanopore.

To estimate total target small molecule concentration, a repeated experiment can be conducted with a nanopore and using two or more different concentrations of surrogate molecules and a constant scaffold/fusion concentration. Different concentrations of surrogate molecules, from low (1 pM) to high (100 nM), can be titrated while using a portion of a common sample conserves the target molecule concentration. By measuring the percentage and the capture rate of flagged-target-positive events, the modeling framework in Wang, Hongyun, et al., *ACS Nano* 7, no. 5 (May 28, 2013), can permit estimation of the total concentration of the target molecule that competes with the known concentration of surrogate molecule. The method can either use a pre-established Kd value for the binding affinity between the target and the target molecule binding domain on the fusion molecule, or permit estimation of this Kd value. To estimate total target small molecule concentration, a multi-nanopore array can also be implemented, with each nanopore will measured a different concentration of scaffold/fusion-surrogate relative to the scaffold/fusion-target to be estimated.

Compositions

In some embodiments, provided herein are surrogate small molecules bound to a payload molecule. In some embodiments, provided herein are surrogate small molecules comprising a payload molecule binding site.

In some embodiments, the payload molecule can be a dendrimer, double stranded DNA, single stranded DNA, a DNA aptamer, a fluorophore, a protein, a polypeptide, a nanorod, a nanotube, fullerene, a PEG molecule, a liposome, or a cholesterol-DNA hybrid, or chemically synthesized compound. In preferred embodiments, the surrogate small molecule and the payload are connected directly or indirectly via a covalent bond, a hydrogen bond, an ionic bond, a van der Waals force, a hydrophobic interaction, a cation-pi interaction, a planar stacking interaction, or a metallic bond, biotin-(strep, neutr, mono) avidin interaction. The payload adds a differentiating characteristic to the surrogate small molecule, and facilitates detection, with the payload bound to the scaffold/fusion-small molecule having a markedly different current signature when passing through the nanopore than the scaffold/fusion-small molecule without a payload. In some embodiments, the payload molecule can bind to another molecule to affect the bulkiness of the molecule, thereby further enhancing the sensitivity of discrimination between scaffold/fusion-small molecule without and with the payload.

In some aspects, the surrogate small molecule comprises a chemical modification that causes or facilitates recognition and binding of a payload molecule. In some embodiments, the surrogate small molecule has sufficient characteristics, e.g., size, length, charge, etc., so that it is adapted to be detected in a nanopore through generation of a recognizable current impedance signature when bound to a scaffold/fusion macromolecule.

In some embodiments, the target small molecule comprises a peptide, insulin, oxytocin, an amino acid, a protein or domain of a protein, nucleotide, oligomers, DNA, RNA, hormones, lipids, cholesterols, metabolites, sugars, glycans, peptidoglycan, polyglycan, saccharides, oligosaccharides, polysaccharides, phospholipids, steroids, chemically synthesized agonist and antagonists, synthesized derivatives (PNA, LNA, BNA), polycyclic aromatic hydrocarbons (PAH), carbon breakdown byproducts, dioxin, cyclohexamide, vitamins, adenosine triphosphate and ATP analogs, neurotransmitters, dopamine, L-dopa, serotonin, metals, electrolytes, organometals, narcotics and narcotic derivatives, hyaluronic acid, retinol. This list is not meant to be exclusive, as the invention provides, in some embodiments, a novel mechanism for detection of any target small molecule capable of competing with a surrogate molecule for binding to a binding site on a fusion molecule.

In some embodiments, a polymer scaffold comprises a negatively or positively charged polymer that translocates through a nanopore upon application of voltage. In some embodiments, a polymer scaffold comprises a cleavable domain or cleavable linker. In some embodiments, a polymer scaffold capable of binding or bound to a fusion molecule comprising a cleavable linker and translocating through a pore upon application of voltage. In some aspects, the polymer scaffold comprises a deoxyribonucleic acid (DNA), a ribonucleic acid (RNA), a peptide nucleic acid (PNA), a DNA/RNA hybrid, or a polypeptide. The scaffold may also be a chemically synthesized polymer, and not a naturally occurring or biological molecule. In a preferred embodiment, the polymer scaffold is dsDNA to allow more predictable signals upon translocation through the nanopore and reduce secondary structure present in ssDNA or RNA. In some embodiments, the polymer scaffold comprises a fusion molecule binding site that may reside on the end of the scaffold, or at both ends of the scaffold. The scaffold and fusion molecule may be connected via a covalent bond, a hydrogen bond, an ionic bond, a van der Waals force, a hydrophobic interaction, a cation-pi interaction, a planar stacking interaction, or a metallic bond. Alternatively, direct covalent tethering of the cleavable linker component to the scaffold may connect the scaffold and the fusion molecule. Alternatively, a connector component of the fusion may join the cleavable linker to the scaffold via direct covalent tethering. In a preferred embodiment, the fusion molecule comprises a scaffold-binding domain can be a DNA, RNA, PNA, polypeptide, a cholesterol/DNA hybrid, or a DNA/RNA hybrid.

In some embodiments, the molecules disclosed herein can be modified or have the capability to bind to a specified entity via a specific binding domain. Molecules, in particular proteins, that are capable of specifically recognizing binding motifs are known in the art. For instance, protein domains such as helix-turn-helix, a zinc finger, a leucine zipper, a winged helix, a winged helix turn helix, a helix-loop-helix and an HMG-box, are known to be able to bind to nucleotide sequences. Any of these molecules may act as a payload molecule binding to the amplicon or primer.

In some aspects, the binding domains can be locked nucleic acids (LNAs), bridged nucleic acids (BNA), Protein Nucleic Acids of all types (e.g. bisPNAs, gamma-PNAs), transcription activator-like effector nucleases (TALENs), clustered regularly interspaced short palindromic repeats (CRISPRs), or aptamers (e.g., DNA, RNA, protein, or combinations thereof).

In some embodiments, the binding domains are one or more of DNA binding proteins (e.g., zinc finger proteins), antibody fragments (Fab), chemically synthesized binders (e.g., PNA, LNA, TALENS, or CRISPR), or a chemical modification (i.e., reactive moieties) in the synthetic polymer scaffold (e.g., thiolate, biotin, amines, carboxylates).

Nanopore Devices

A nanopore device, as provided, includes at least a pore that forms an opening in a structure separating an interior space of the device into two volumes, and at least a sensor configured to identify objects (for example, by detecting changes in parameters indicative of objects) passing through the pore. Nanopore devices used for the methods described herein are also disclosed in PCT Publication WO/2013/012881, incorporated by reference herein in its entirety.

Sensors

As discussed above, in various aspects, the nanopore device further includes one or more sensors to carry out the detection of the target small molecule.

The sensors used in the device can be any sensor suitable for identifying a target polynucleotide amplicon bound or unbound to a payload molecule. For instance, a sensor can be configured to identify the polymer scaffold/fusion molecule complex bound to a surrogate molecule or a target small molecule by measuring a current, a voltage, a pH value, an optical feature, or residence time associated with the polymer. In other aspects, the sensor may be configured to identify one or more individual components of the polymer scaffold/fusion complex or one or more components bound or attached to the polymer scaffold/fusion molecule complex (e.g., the surrogate molecule or the target small molecule). The sensor may be formed of any component configured to detect a change in a measurable parameter where the change is indicative of entity bound to the complex, a component of the complex, or preferably, a component bound or attached to the complex. In one aspect, the sensor includes a pair of electrodes placed at two sides of a pore to measure an ionic current across the pore when a molecule or other entity moves through the pore. In certain aspects, the ionic current across the pore changes measurably when a polymer scaffold/fusion molecule segment passing through the pore is bound to a surrogate molecule or a target molecule. Such changes in current may vary in predictable, measurable ways corresponding with, for example, the presence, absence, and/or size of the surrogate molecule (and bound entities) or target small molecule bound to the polymer scaffold/fusion molecule complex.

In a preferred embodiment, the sensor comprises electrodes that apply voltage and are used to measure current across the nanopore. Translocations of molecules through the nanopore provides electrical impedance (Z) which affects current through the nanopore according to Ohm's Law, V=IZ, where V is voltage applied, I is current through the nanopore, and Z is impedance. Inversely, the conductance G=1/Z are monitored to signal and quantitate nanopore events. The result when a molecule translocates through a nanopore in an electrical field (e.g., under an applied voltage) is a current signature that may be correlated to the molecule passing through the nanopore upon further analysis of the current signal.

When residence time measurements from the current signature are used, the size of the component can be correlated to the specific component based on the length of time it takes to pass through the sensing device.

In one embodiment, a sensor is provided in the nanopore device that measures an optical feature of the polymer, a component (or unit) of the polymer, or a component bound or attached to the polymer. One example of such measurement includes the identification of an absorption band unique to a particular unit by infrared (or ultraviolet) spectroscopy. In some embodiments, the sensor is an electric sensor. In some embodiments, the sensor detects a fluorescent signature. A radiation source at the outlet of the pore can be used to detect that signature.

EXAMPLES

The present technology is further defined by reference to the following example and experiments. It will be apparent to those skilled in the art that many modifications may be practiced without departing from the scope of the current invention.

Example 1

Nanopore Detection of DNA

A solid-state nanopore is a nano-scale opening formed in a thin solid-state membrane that separates two aqueous volumes. A voltage-clamp amplifier applies a voltage V across the membrane while measuring the ionic current through the open pore. Unlike any other single-molecule sensor, the nanopore device can be packaged into a handheld form factor at very low cost. When a single charged molecule such as a double-stranded DNA (dsDNA) is captured and driven through the pore by electrophoresis, the measured current shifts, and the conductance shift depth ($\delta G = \delta I/V$) and duration are used to characterize the event (FIG. 4(a)).

The value $\delta G$ (also labeled $\Delta G$) can be computed as the mean current shift divided by voltage. The value $\delta G$ (also labeled $\Delta G$) can also be computed as the maximum current shift divided by voltage. The duration is computed as the shift width.

We placed 0.1 nM 3.2 kb dsDNA into a nanopore device with a 27 nm diameter nanopore. The solution in the nanopore device comprised 1M LiCl. We applied a voltage of 100 mV across the nanopore to induce translocation of the dsDNA across the nanopore. Events were detected by the current sensor and analyzed as described below.

Figure 4:
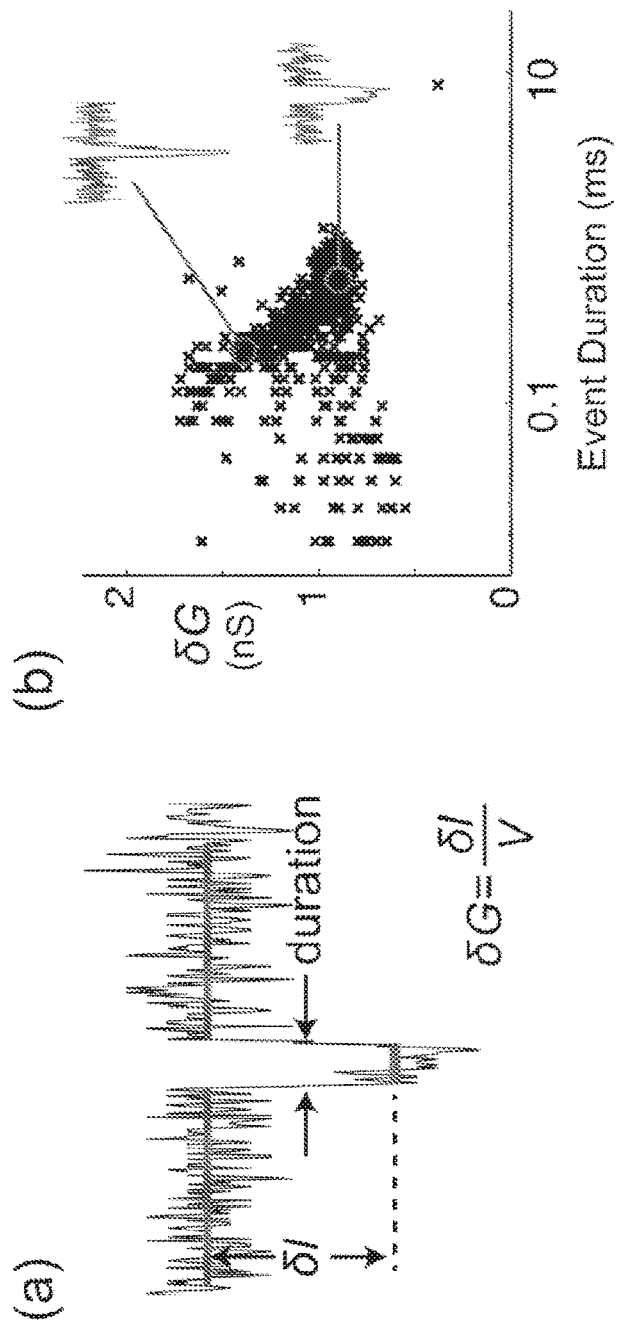
FIG. 4 demonstrates single-molecule sensing with a nanopore device. (a) A representative current-shift event caused by a 3.2 kb dsDNA scaffold passing through a 27 nm diameter nanopore at voltage V=100 mV (1M LiCl). Events are quantitated by conductance shift depth ($\delta G=\delta I/V$) and duration. (b) Scatter plot of $\delta G$ versus duration for 744 events recorded over 10 minutes.

After recording many events during an experiment, distributions of the events are analyzed to characterize the corresponding molecule. FIG. 4(b) shows the event characteristics for 0.1 nM of 3.2 kb dsDNA passing through an 27 nm diameter nanopore at voltage V=100 mV (1M LiCl), producing 744 events recorded in 10 minutes. The two encircled representative events show: a wider and shallower event corresponding to the DNA passing through unfolded; and a faster but deeper event corresponding to the DNA passing through folded. For dsDNA that is ~1 kb and shorter, the DNA passes through the pore only in an unfolded state.

Example 2

Competition Assay Varying Target and Surrogate Molecules

To demonstrate our competition assay method, a dsDNA scaffold (i.e., the polymer scaffold) with a single bisPNA molecule (i.e., the fusion molecule) was used. The bisPNA was cysteine-tagged to react with and bind to varying concentrations of small N-ethyl maleimide (NEM) (i.e., the target small molecule) in competition with varying preselected amounts of 10 kDa maleimide polyethylene glycol (PEG-mal) (i.e., the surrogate molecule). The relative ratios of target:surrogate analyzed were 1:1 and 1:4.

The methods of reagent preparation were as follows: A solution of 25 μM cysteine-tagged bis peptide nucleic acid (bisPNA) was mixed with and allowed to react with varying selected concentrations of the small molecule N-ethyl maleimide (NEM, 125 g/mol) and/or 10 kDa maleimide polyethylene glycol (PEG-mal, 10,000 g/mol) for a period of 20 minutes at room temperature. The conjugation was carried out in bisPNA binding buffer (0.01M sodium phosphate, pH 7.4).

Following the brief incubation, the reaction products were analyzed by reverse phase HPLC (Agilent 1100 series) to confirm the composition of the NEM-bisPNA and/or PEG-bisPNA conjugates. In RP-HPLC, analytes were eluted from a non-polar stationary phase by increasing concentrations of an organic mobile phase over time and identified by their characteristic absorbance spectra. The peak absorbances for the respective reactants were 220 nm (10 kDa PEG-maleimide), 270 nm (PNA), and 303 nm (NEM). Because PNA gives the strongest signal of the reactants, it was used in all competition experiments to monitor progression of the resulting reaction products of PNA-NEM and/or PNA-PEG.

Figure 5A:
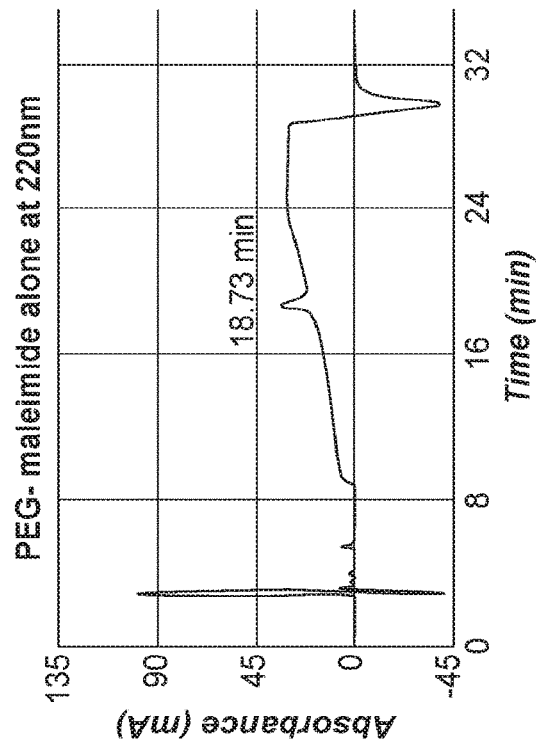
FIGS. 5A, 5B and 5C show a characterization of individual reactants by RP-HPLC to use as reference controls for subsequent competition reactions.
Figure 5B:
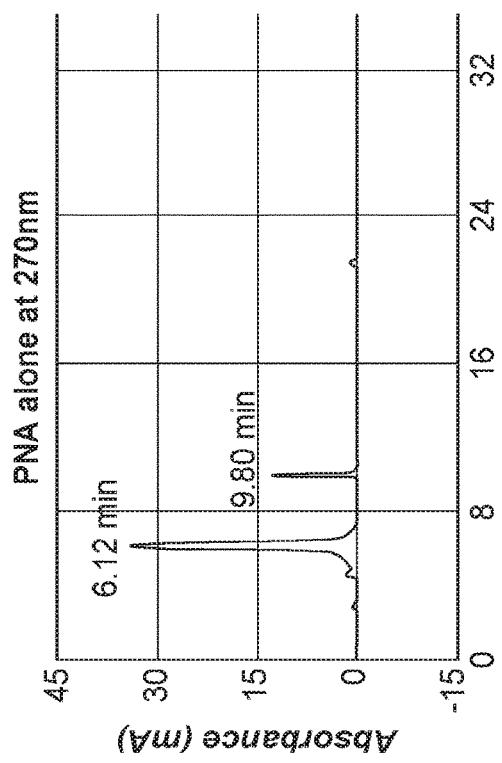
Figure 5C:
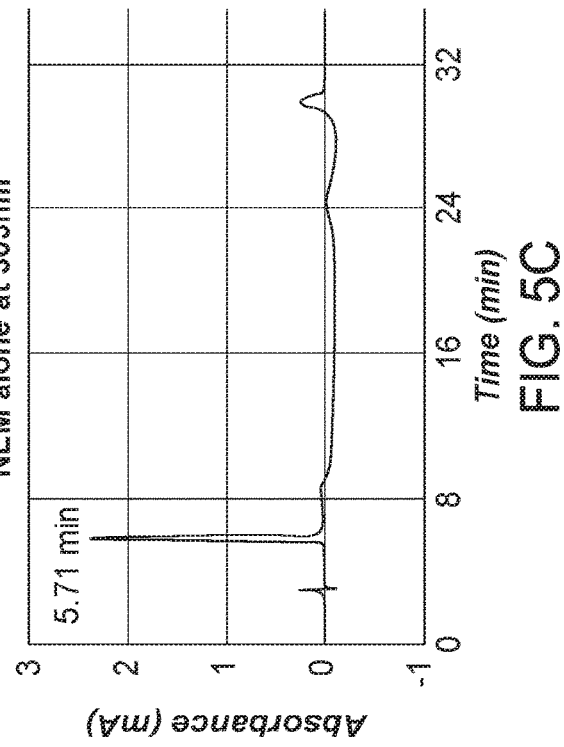

The elution time and absorbance spectra of individual reactants alone were first characterized by RP-HPLC to be used as reference controls for subsequent competition reactions (FIGS. 5A, 5B and 5C). PNA eluted at 6.12 minutes and exhibited strong absorbance at 270 nm (FIG. 5A). A peak also eluted at 9.80 minutes that was determined to be an impurity in the PNA provided from the manufacturer, and did not participate in any of the following reactions. The PEG-maleimide molecule by itself gave a small, broad peak at 18.73 min (FIG. 5B) while NEM alone gave a very small peak at 5.71 min (FIG. 5C). Because of the weak signals given off by the competing molecules PEG and NEM, the disappearance of PNA absorbance at 6.12 minutes and the appearance of new PNA peaks elsewhere with strong 270 nm absorbance was then used as an indicator of successful PNA coupling.

Figure 6:
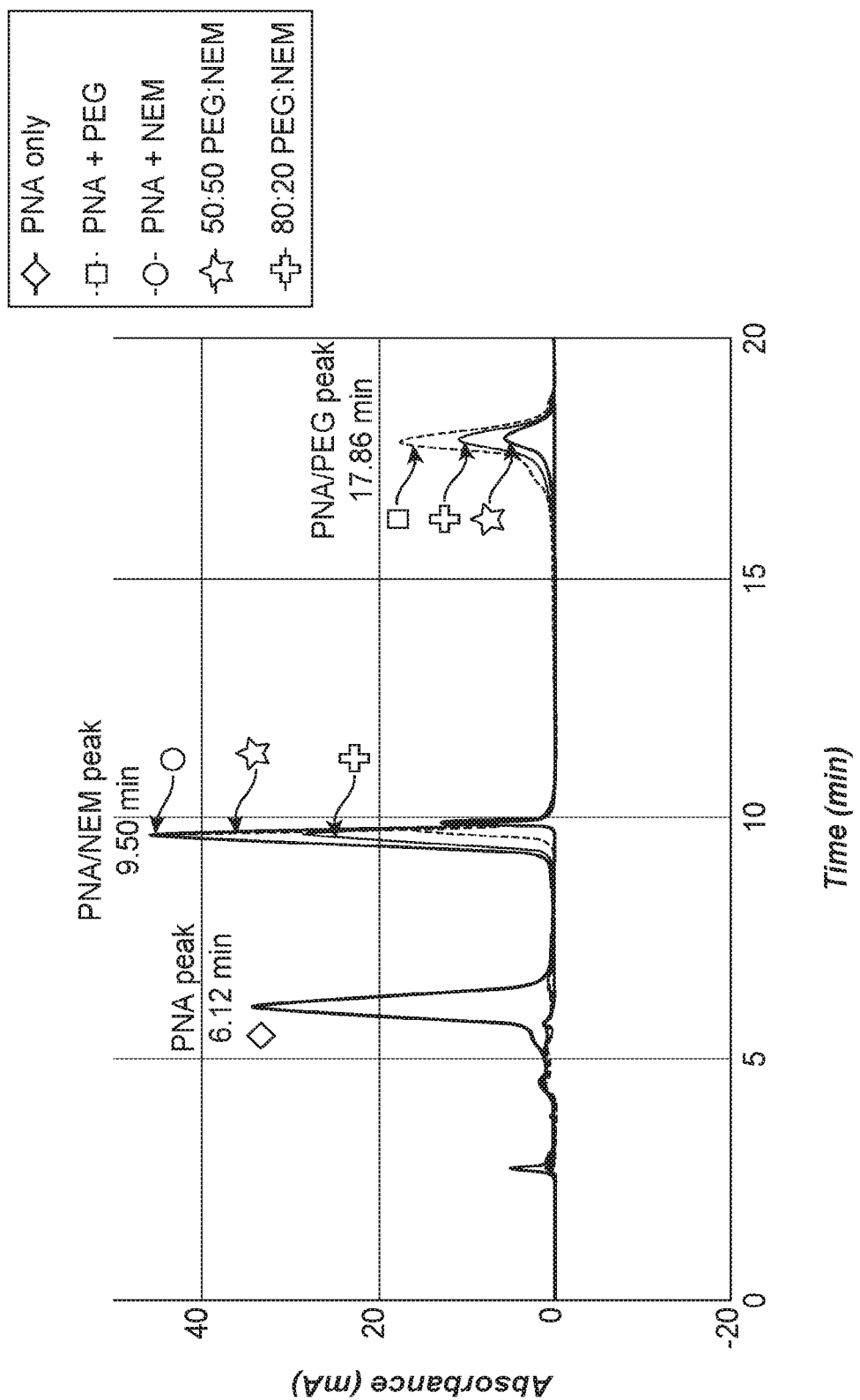
FIG. 6 shows a characterization of the products of incubation of cysteine-labeled PNA molecules with varying concentrations of excess PEG-maleimide and/or NEM by RP-HPLC to verify complex formation and assess the results of competitive binding to the PNA molecule.

When PNA was incubated with PEG-maleimide alone, the PNA absorbance normally detected at an elution time of 6.12 min that is indicative of uncoupled PNA (FIG. 6, solid diamond) disappeared, and a new molecule with a strong absorbance at 270 nm eluted at 17.86 min indicating the formation of a PNA-PEG conjugate (FIG. 6, solid square). Similarly, when PNA was allowed to incubate with NEM alone, the PNA fully reacted with the molecule and a new peak appeared at 9.5 minutes (FIG. 6, open circle). PEG and NEM were also allowed to react with PNA at equimolar and 4:1 PEG to NEM ratios (FIG. 6, solid star and solid cross). The intensity value of the peak at 17.86 min decreases across samples as NEM concentration is increased relative to PEG, indicating that NEM is able to successfully compete for the thiol reactive group of the cysteine-tagged PNA molecule.

Figure 7:
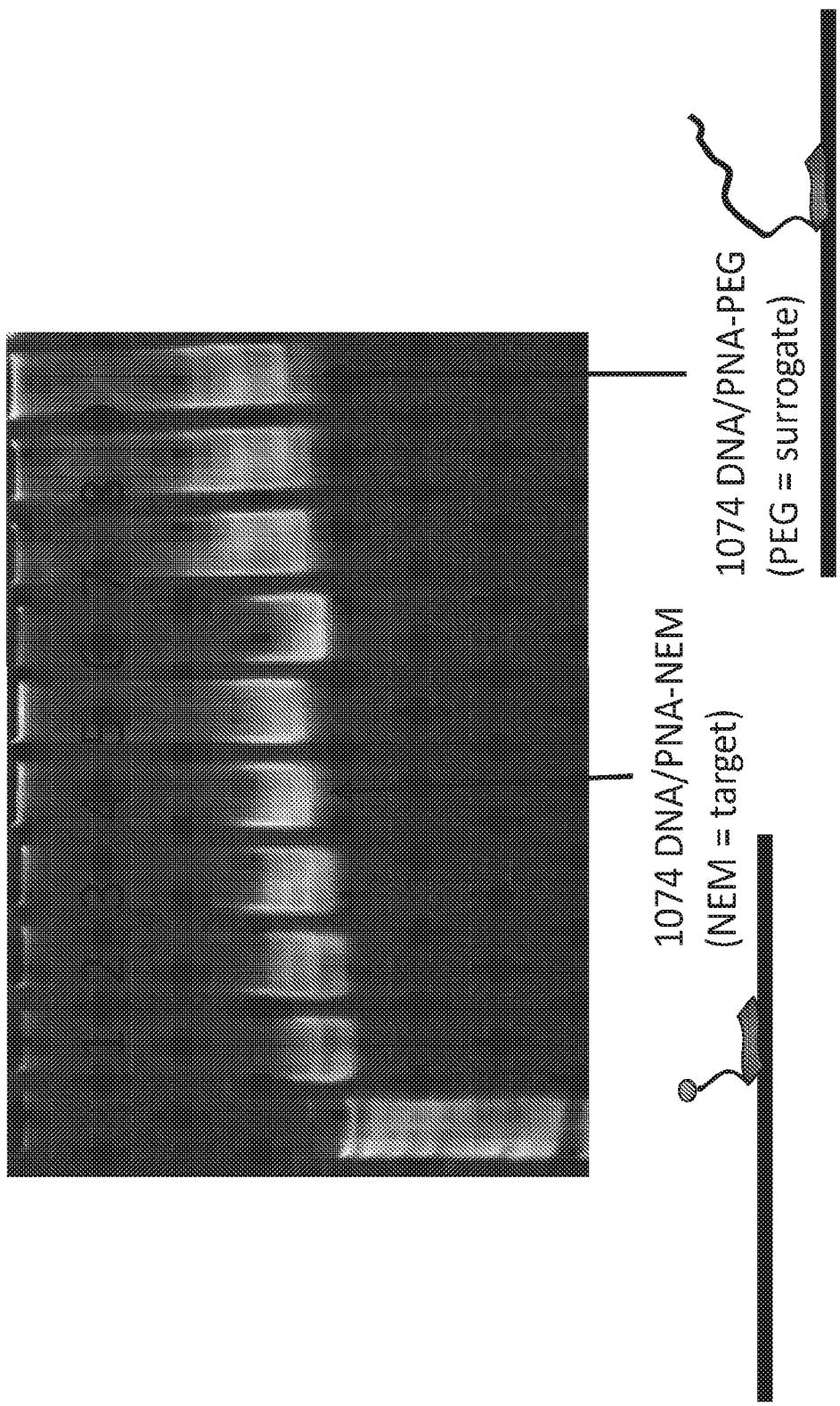
FIG. 7 shows a gel comparing the electrophoretic mobility of the scaffold/fusion-target (lane 4) and scaffold/fusion-surrogate complexes (lane 9) tested with the nanopore, where NEM is the target and PEG is the surrogate, with each competing for a binding site on a PNA that binds to the DNA scaffold.

The NEM-PNA and/or PEG-PNA complexes were mixed with a 1074 bp double-stranded DNA (dsDNA) fragment for a period of 2 hours at 60° C. in bisPNA binding buffer to allow formation of the polymer scaffold/fusion molecule complex (i.e., binding of the dsDNA to the bisPNA conjugates). Scaffold-fusion molecule binding complexes were confirmed by an electrophoretic mobility shift assay on a 5% polyacrylamide gel (FIG. 7). Specifically, a 5% polyacrylamide gel was run to assess the binding of dsDNA by a PNA molecule tagged (i.e., bound) with either NEM (target) or 10 kDa PEG (surrogate). Bare 1074 bp dsDNA (FIG. 7, Lane 1) was allowed to incubate with increasing amounts of NEM-bound PNA ranging from a 10 to 100-fold molar excess of NEM-bound PNA relative to DNA (FIG. 7, Lanes 2 through 5). A 50-fold molar excess of NEM-bound PNA was found to be sufficient to fully label the 1074 bp sequence (FIG. 7, lane 4), and was therefore used in subsequent nanopore analysis. PEG-tagged PNA was similarly allowed to bind to dsDNA at concentrations ranging from 10 to 50-fold molar excess (FIG. 7, Lanes 7-9). The sample used for nanopore analysis was the sample where all DNA present was bound to the PEG labeled PNA (FIG. 7, Lane 9, 50-fold molar excess).

Once verified, the polymer scaffold/fusion complexes bound to NEM or PEG-mal were diluted to the indicated concentration in running buffer (1M LiCl, 10 mM Tris, 1 mM EDTA, pH 8) for nanopore analysis. All reagents in Example 1 were tested serially on the same 20-22 nm diameter pore in a 22 nm membrane. Buffer only flushes were used in between testing of each reagent type.

Figure 8:
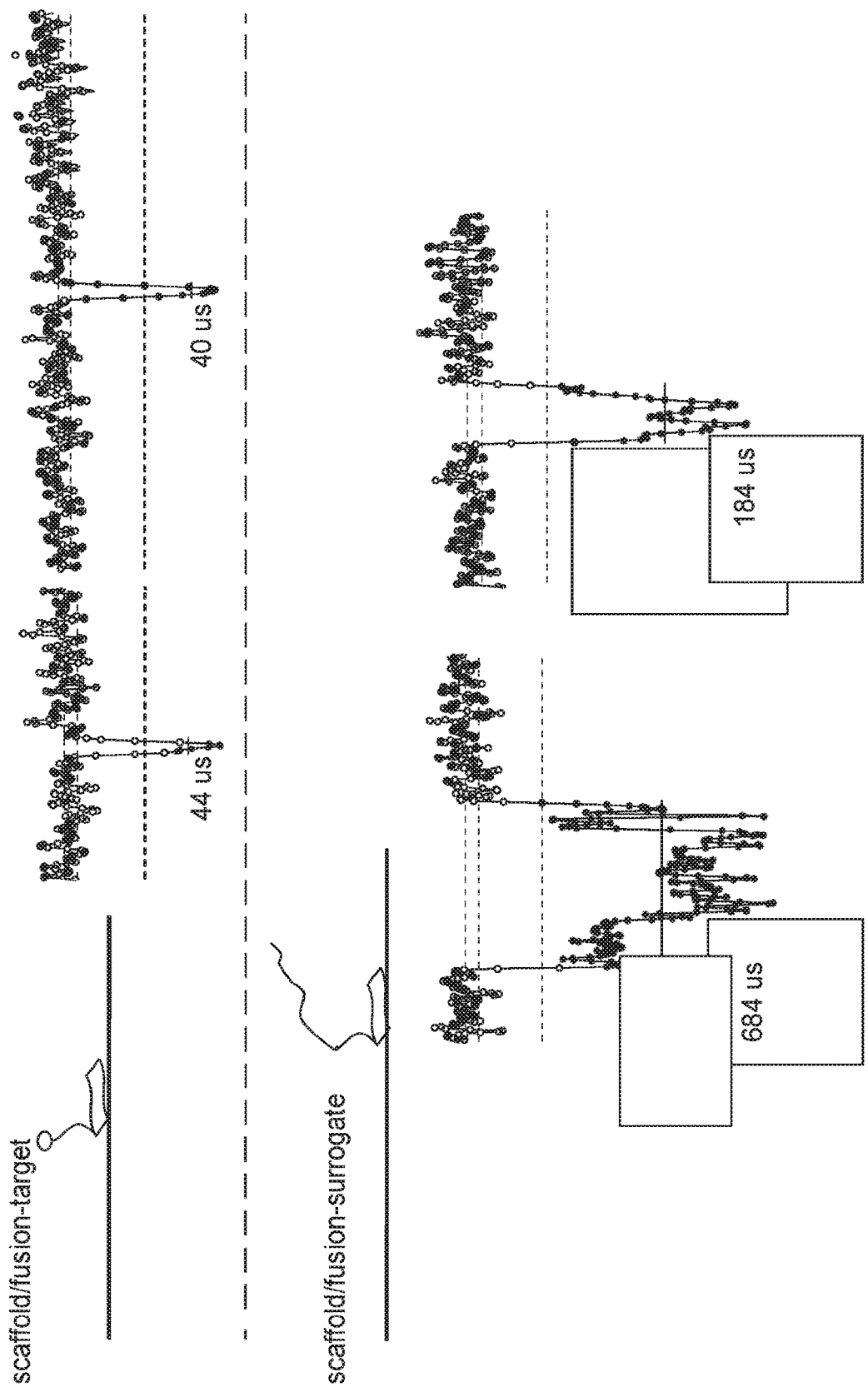
FIG. 8 shows recorded representative events for scaffold/fusion-target and scaffold/fusion-surrogate complexes, where NEM is the target and PEG is the surrogate. The added payload size of the surrogate creates a deeper and longer lasting event signature.
Figure 9:
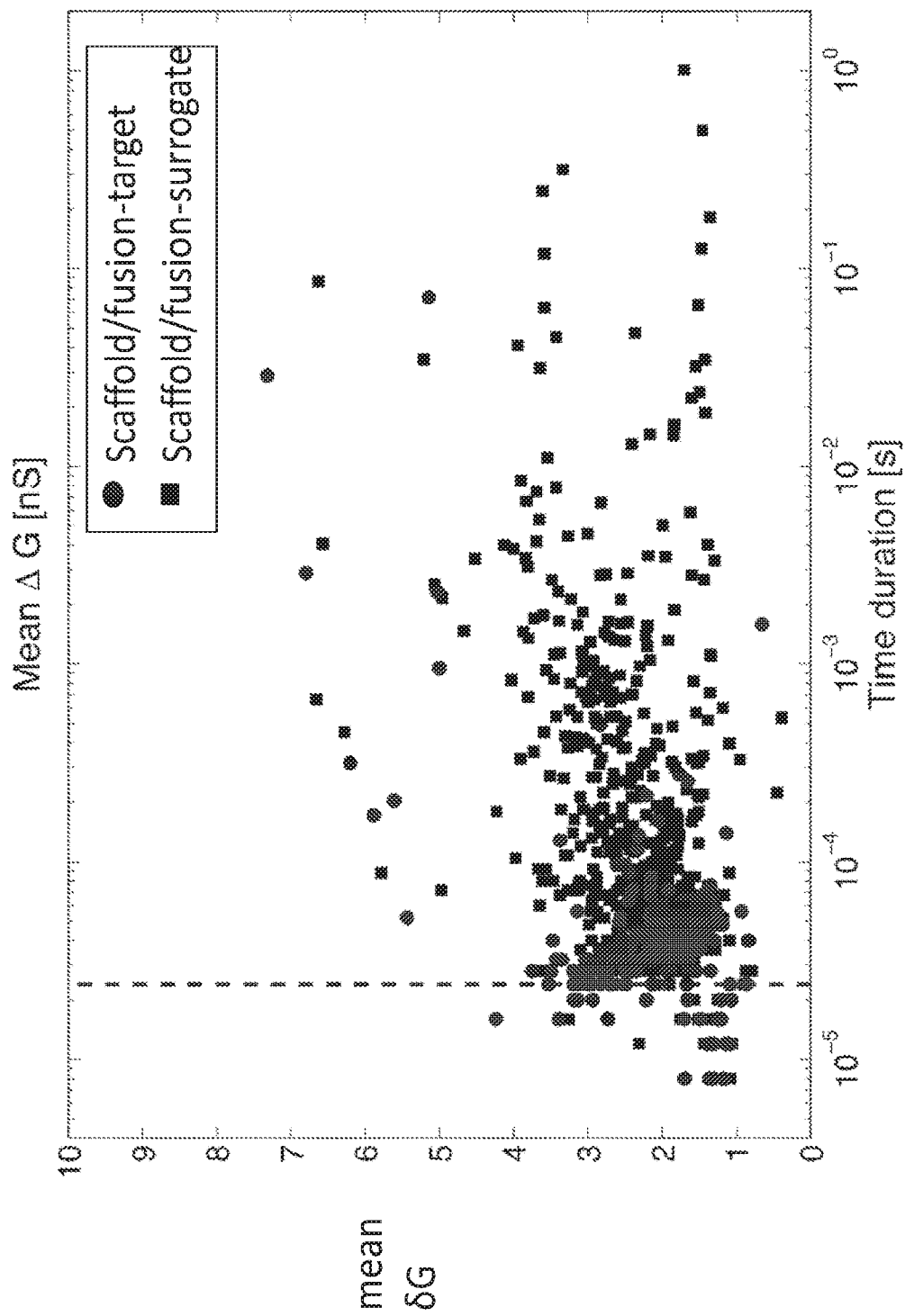
FIG. 9 shows the scatter plot of mean δG versus duration for all scaffold/fusion-target events and then all scaffold/fusion-surrogate events recorded on the same pore.

First, the DNA/PNA-NEM complexes at 0.5 nM produced 346 events over 17 minutes. Most events were faster than 100 µs, with median dwell (IQR (interquartile range)) =44 (20) µsec, as seen in FIGS. 8 and 9. The capture rate was 0.33 sec$^{-1}$ ($R^2$=0.9973). Subsequently, 1074 DNA+PNA+PEG was measured at 0.5 nM and produced 651 events over 20 minutes. Many events were longer than 100 µs, with median dwell (IQR)=72 (275) µsec, as seen in FIGS. 8 and 9. The capture rate was 0.68 sec$^{-1}$ ($R^2$=0.9985).

By applying the framework established in the section "Assigning Statistical Significance to Detection," we assigned statistical confidence to detecting the DNA/PNA-NEM complex as the type 2 molecule and DNA/PNA-PEG as the type 1 molecule. A suitable criterion is to tag an event as type 2 if it is faster than 0.1 ms. The DNA/PNA-PEG can be used as the negative control, to compute the false positive q1=0.585 (58.8%). The DNA/PNA-NEM (type 2) control produced $Q(p) \pm Qs_{sd}(p)$=94.7977±3.0752 at 99% confidence. From equation (1) of the mathematical framework, the result is $Q(p)-Q_{sd}(p)$=0.917>0.585, which means we can say that DNA/PNA-NEM molecules are present with 99% confidence.

Figure 10:
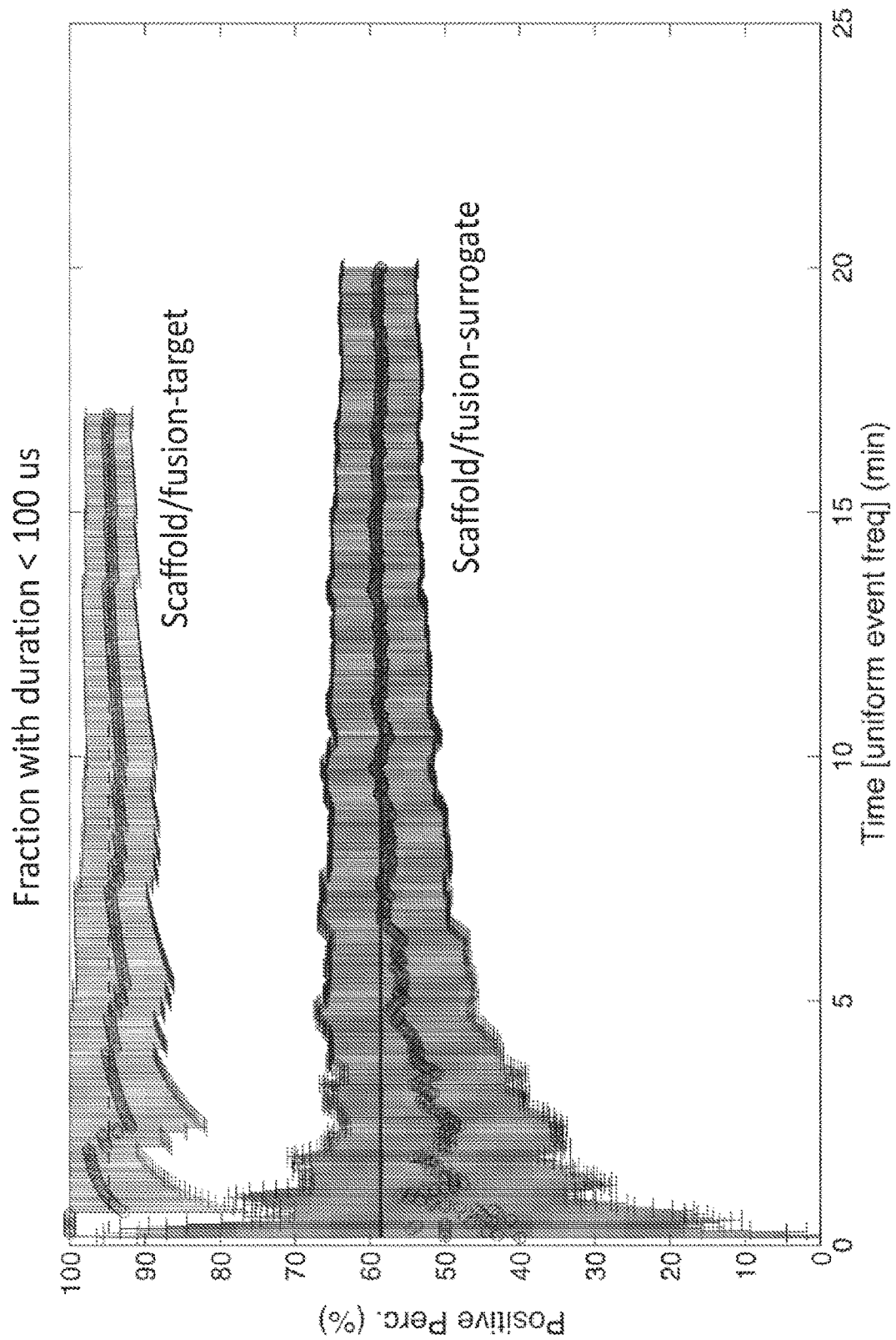
FIG. 10 shows the evolution of the percentage of events with duration below 100 μs, recorded over time, from the populations in FIG. 7. The error bars indicate the uncertainty in the measured percentage.

A plot of $Q(p) \pm Q_{sd}(p)$ as a function of recording time is shown for each reagent type (DNA/PNA-NEM and DNA/PNA-PEG) in FIG. 10. Observe that DNA/PNA-NEM complexes (Scaffold/fusion-target) were detected with 99% confidence within the first minute of recording.

We next varied the PEG:NEM ratios at 80:20 and 50:50 to assess how competition for the bisPNA binding sites would translate in the nanopore measurements.

Figure 11:
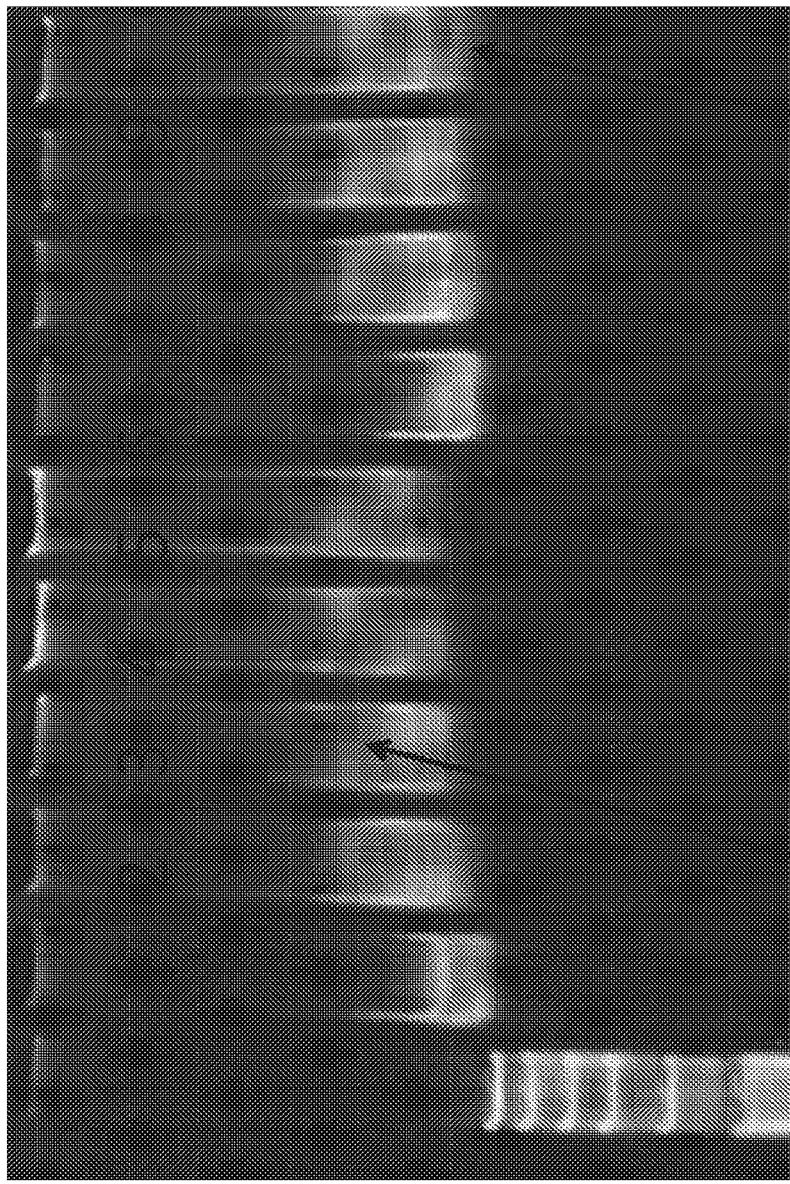
FIG. 11 shows a gel comparing the electrophoretic mobility of the scaffold/fusion-target and scaffold/fusion-surrogate complexes with a surrogate:target competition ratio of 1:1 (lane 3) and 4:1 (lane 9), with both tested on the nanopore. As before, NEM is the target and PEG is the surrogate, with each competing to bind to a PNA that binds to the DNA scaffold.

The binding of dsDNA by a solution of PNA molecules tagged with NEM (target) and 10 kDa PEG (surrogate) was detected on a 5% polyacrylamide gel (FIG. 11). A solution of PNA that was previously reacted with equimolar amounts of PEG and NEM (1:1) was mixed with a 1074 bp dsDNA fragment (i.e., polymer scaffold) in 10 to 100-fold molar excess PNA relative to DNA (FIG. 9, Lanes 2-5) in order to bind the PNA molecules to the dsDNA. Nanopore analysis was conducted on the sample in which each DNA molecule is bound to the PNA tagged molecules (FIG. 11, Lane 3). PNA was also mixed with a solution of PEG and NEM in which PEG outnumbered NEM by a 4:1 molar ratio. This solution of tagged PNA molecules was subsequently allowed to invade DNA in a similar fashion, (Lanes 7-9, 10 to 50-fold molar excess). Nanopore analysis was conducted on the sample in which each DNA molecule is bound to the PNA tagged molecules (FIG. 11, Lane 9).

Figure 12:
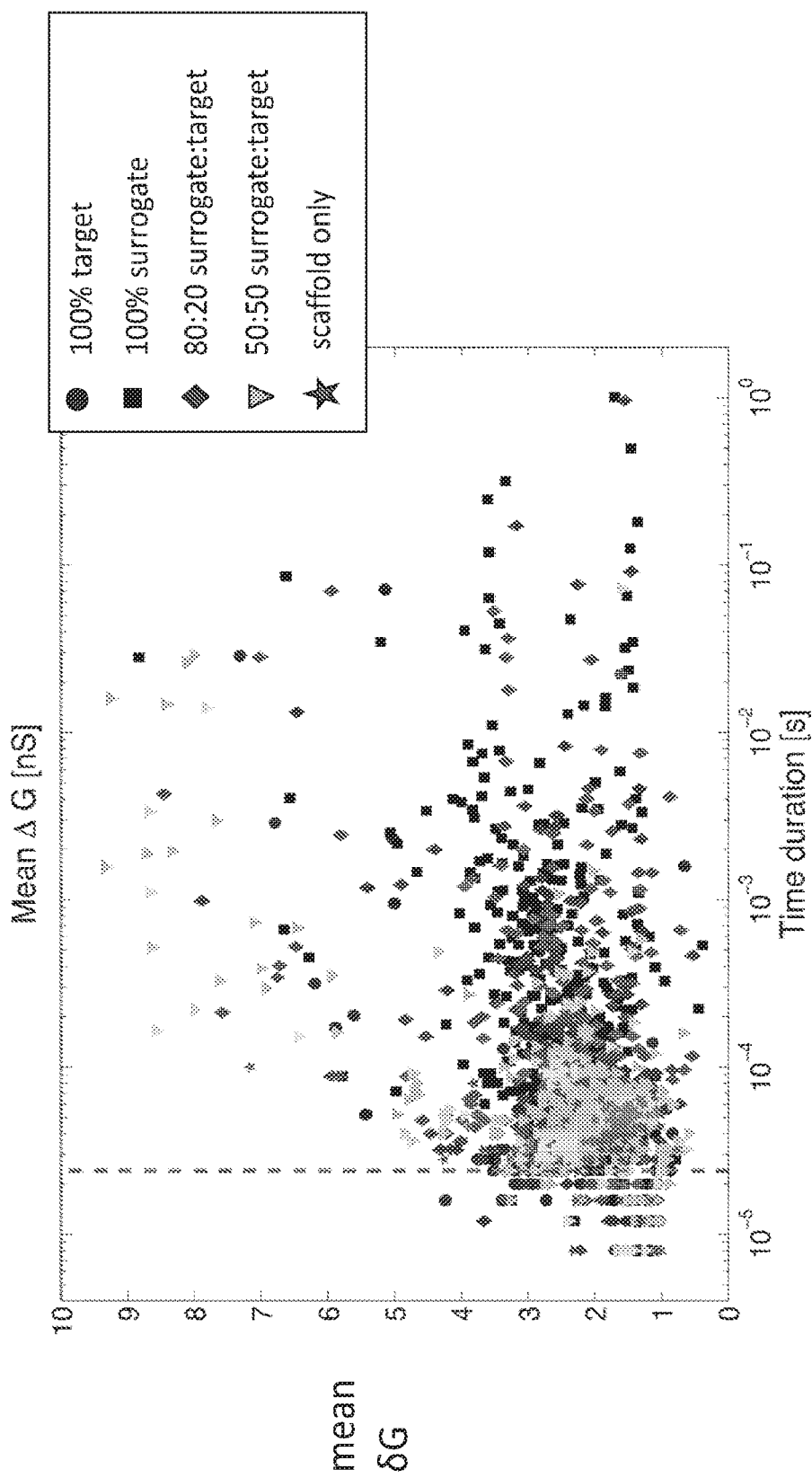
FIG. 12 shows the scatter plot of δG versus duration for 100% scaffold/fusion-target and 100% scaffold/fusion-surrogate complexes, and also scaffold/fusion following incubation with surrogate:target (PEG:NEM) competition ratios of 4:1 and 1:1. All reagent types were recorded serially on the same pore, with flushing in between measurements.
Figure 13:
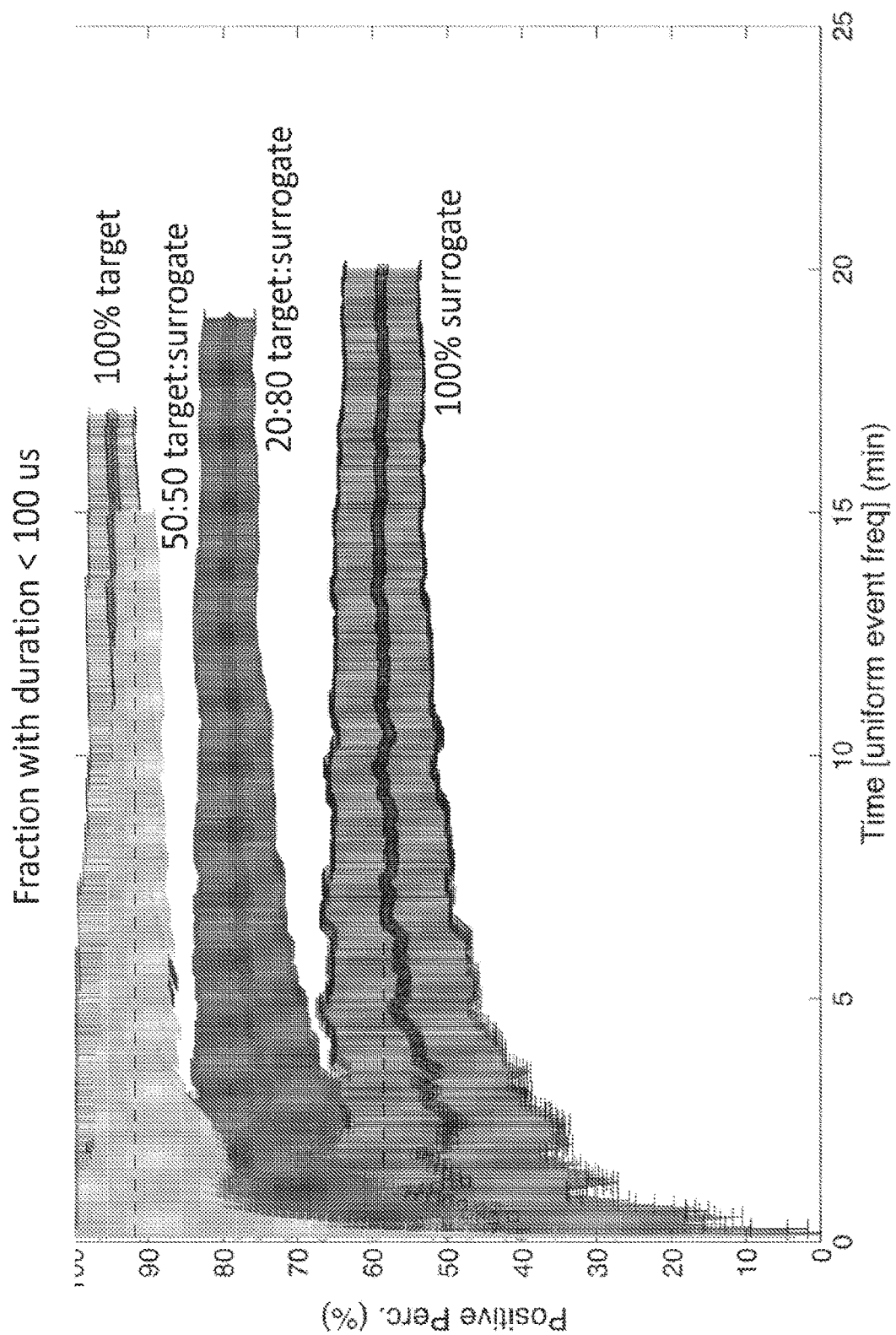
FIG. 13 shows the evolution of the percentage of events with duration below 100 μs, recorded over time, from the populations in FIG. 10. The error bars quantitate the uncertainty in the measured percentage. The increase in events faster than 100 μs is indicative of an increasing fraction of target small molecules binding to scaffold/fusion complexes compared to surrogate molecules.

First, 0.2 nM 1074 DNA/PNA+PEG:NEM=80:20 produced 952 events over 19 minutes with a median dwell (IQR)=56 (44) µsec and a capture rate of 1.0 sec$^{-1}$ ($R^2$=0.9984). The fraction of events faster than 0.1 ms was $Q(p) \pm Q_{sd}(p)$=79.0966+/−3.3946 at 99% confidence. Subsequently, 0.2 nM 1074 DNA/PNA+PEG:NEM=50:50 produced 754 events over 15 minutes with a median dwell (IQR)=48 (20) µs and a capture rate of 0.951 sec$^{-1}$ ($R^2$=0.9978). The fraction of events faster than 0.1 ms increased to $Q(p) \pm Q_{sd}(p)$=91.7772+/−2.577 at 99% confidence, as the relative amount of NEM to PEG was increased. FIG. 12 shows the events plot for the DNA/PNA-NEM and DNA/PNA-PEG controls and the DNA/PNA+PEG:

NEM=80:20 and DNA/PNA+PEG:NEM=50:50 overlaid. A DNA only control is also shown. FIG. 13 shows a plot of $Q(p) \pm Q_{sd}(p)$ as a function of recording time for each reagent type in FIG. 12. The trend of increasing fraction as the relative amount of NEM to PEG increases shows that competition between NEM and PEG is detectable with the nanopore. Such measurements can be used to detect the presence of the target small molecule, as shown here for NEM and with 99% confidence. Such measurements can also be combined with biophysical models to estimate the target small molecule concentration.

Example 3

Competition Assay with Fixed Surrogate and Varying Target Molecules

As in Example 2, a dsDNA scaffold with a single bisPNA molecule was used, with the cysteine-tagged bisPNA mixed with varying concentrations of small N-ethyl maleimide (NEM) as the model target small molecule and a constant amount of the model surrogate 10 kDa maleimide polyethylene glycol (PEG-mal). The surrogate and the target small molecule were in competition for binding to the cysteine-tagged bisPNA. The concentration of the surrogate molecule was constant, in contrast with example 2 in which both the target and the surrogate were varied. The relative ratios of target:surrogate explored in this example are 1:2 and 1:10 and 1:50. The formed complexes from each mixture were analyzed using a nanopore 20-22 nm in diameter and with a 22 nm membrane.

The methods of reagent preparation were as follows: A solution of 25 μM cysteine-tagged bisPNA was mixed with 250 μM 10 kDa PEG-mal and varying concentrations of NEM for a period of 20 minutes at room temperature in bisPNA binding buffer to allow binding of the PEG-mal or NEM to each cysteine-tagged bisPNA.

Following the brief incubation, the reaction products were analyzed by reverse phase HPLC (Agilent 1100 series) to confirm the composition of the NEM-bisPNA and/or PEG-bisPNA conjugates. The elution time and absorbance spectra of individual reactants alone were first characterized by RP-HPLC to be used as reference controls for subsequent competition reactions (FIGS. 5A, 5B and 5C). PNA eluted at 6.12 minutes and exhibited strong absorbance at 270 nm (FIG. 5A). A peak also eluted at 9.80 minutes that was determined to be an impurity in the PNA provided from the manufacturer, and did not participate in any of the following reactions. The PEG-maleimide molecule by itself gave a small, broad peak at 18.73 min (FIG. 5B) while NEM alone gave a very small peak at 5.71 min (FIG. 5C). Because of the weak signals given off by the competing molecules PEG and NEM, the disappearance of PNA absorbance at 6.12 minutes and the appearance of new PNA peaks elsewhere with strong 270 nm absorbance was then used as an indicator of successful PNA coupling.

Figure 14:
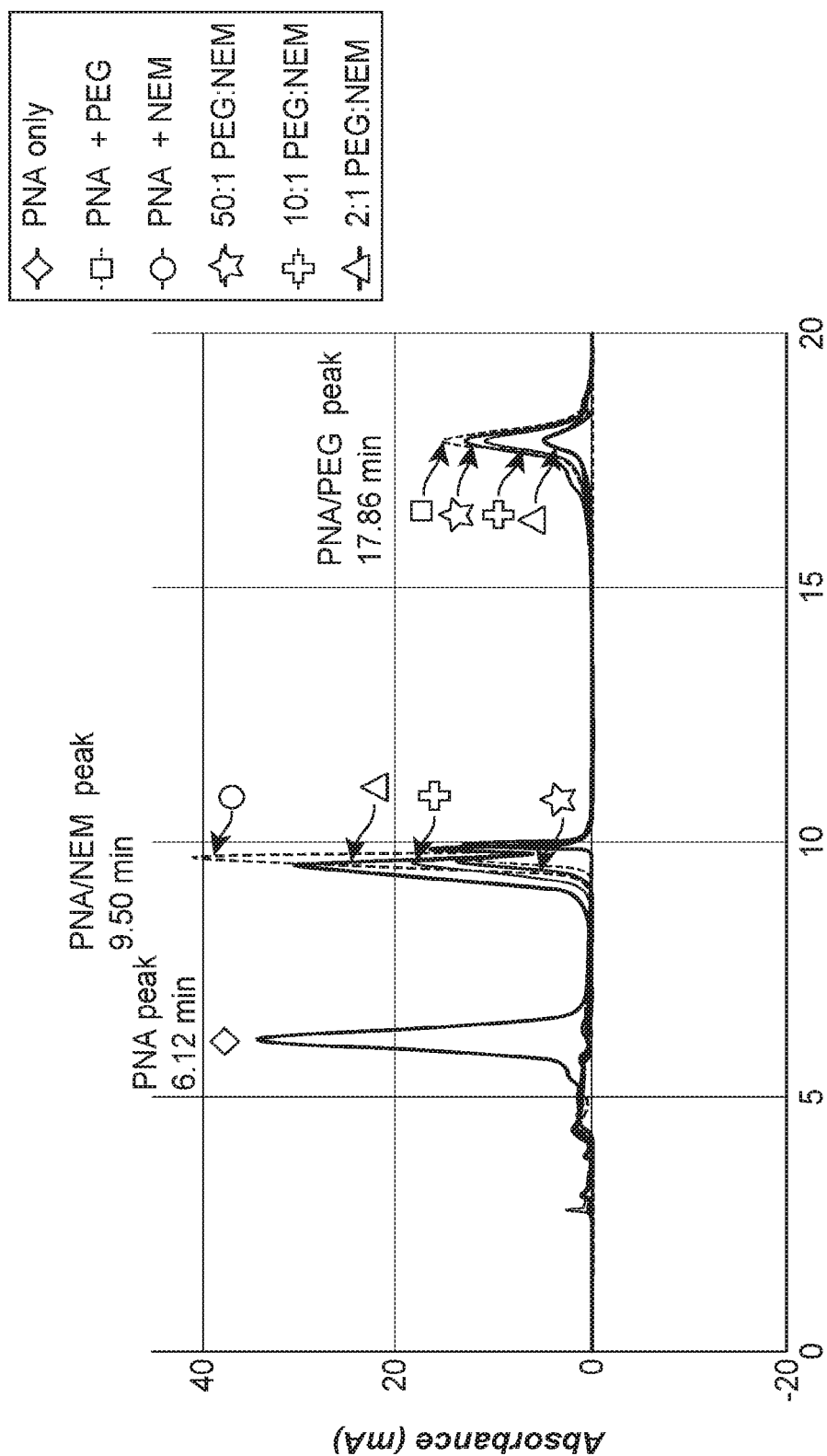
FIG. 14 shows a characterization of the products of incubation of cysteine-labeled PNA molecules with a fixed concentration of PEG-maleimide varying concentrations of NEM by RP-HPLC to verify complex formation and assess the results of competitive binding to the PNA molecule.

PNA was also incubated with a fixed amount of PEG while titrating up target molecule NEM to demonstrate competition for the thiol reactive group of cysteine utilizing a differing experimental design. First, 250 μM of PEG alone was incubated with 25 μM PNA, and a clear peak was detected at 17.86 min (FIG. 14, filled square). In separate reactions NEM was then titrated up from 5 μM (FIG. 14, filled star) to 125 uM (FIG. 14, empty triangle) in the presence of 250 μM PEG. As more NEM was added, a clear reduction in the PNA-PEG peak at 17.86 minutes was seen, while an increase in the peak at 9.5 minutes indicative of the PNA-NEM conjugate was detected. Taken together, these results indicate that the target molecule NEM is able to successfully compete with the thiol reactive group.

The NEM-PNA and/or PEG-PNA complexes were mixed with a 1074 bp dsDNA fragment for a period of 2 hours at 60° C. in bisPNA binding buffer to allow binding of the cysteine-tagged bisPNA fusion molecule to the dsDNA polymer scaffold.

Figure 15:
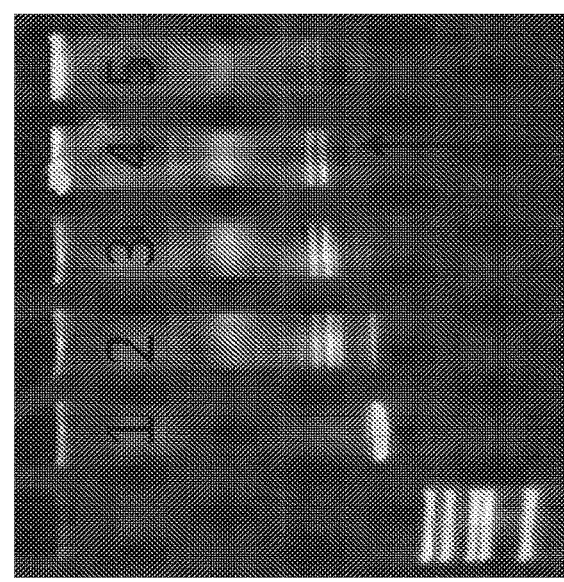
FIG. 15 shows a gel comparing the electrophoretic mobility of the scaffold/fusion-target ((a), lane 4) and scaffold/fusion-surrogate complexes ((b), lane 4) tested with the nanopore, where NEM is the target and PEG is the surrogate, with each competing for a binding site on a PNA that binds to the DNA scaffold.
Figure 15:
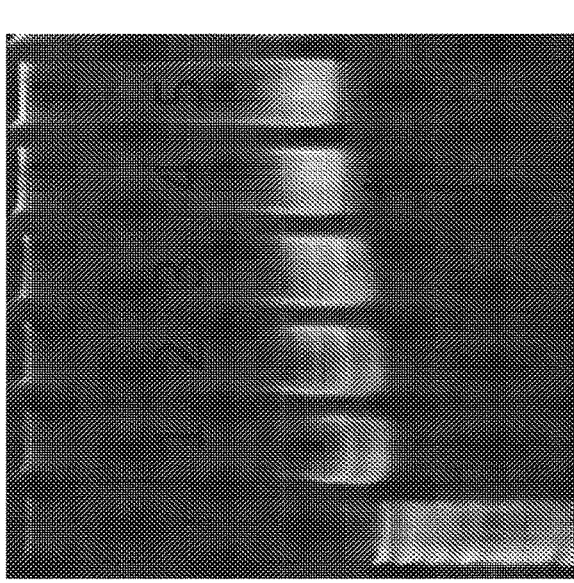
Figure 15:
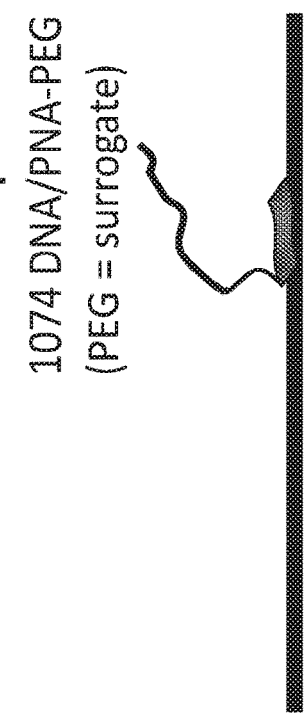

The results of the incubation were observed via an electrophoretic mobility shift assay on a 5% polyacrylamide gel (FIG. 15). Specifically, FIG. 15(a) shows a 5% polyacrylamide gel run to assess the binding of dsDNA to a PNA molecule tagged with NEM (target). Bare 1074 bp dsDNA ((a), Lane 1) was allowed to incubate with increasing amounts of NEM labeled PNA ranging from a 10 to 100-fold molar excess of labeled PNA relative to DNA ((a), Lanes 2-5). A 50-fold molar excess of NEM-tagged PNA was found to be sufficient to fully label the 1074 bp sequence, and was therefore used in subsequent nanopore analysis ((a), Lane 4). FIG. 12(b) shows a 10% polyacrylamide gel that was run to assess the binding of dsDNA to a PNA molecule that had been conjugated with 10 kDa PEG (surrogate). 1074 bp DNA was similarly incubated with increasing concentrations of PNA-PEG, and the sample in which each DNA molecule was bound to PNA was used in the nanopore analysis ((b), Lane 4).

Figure 16:
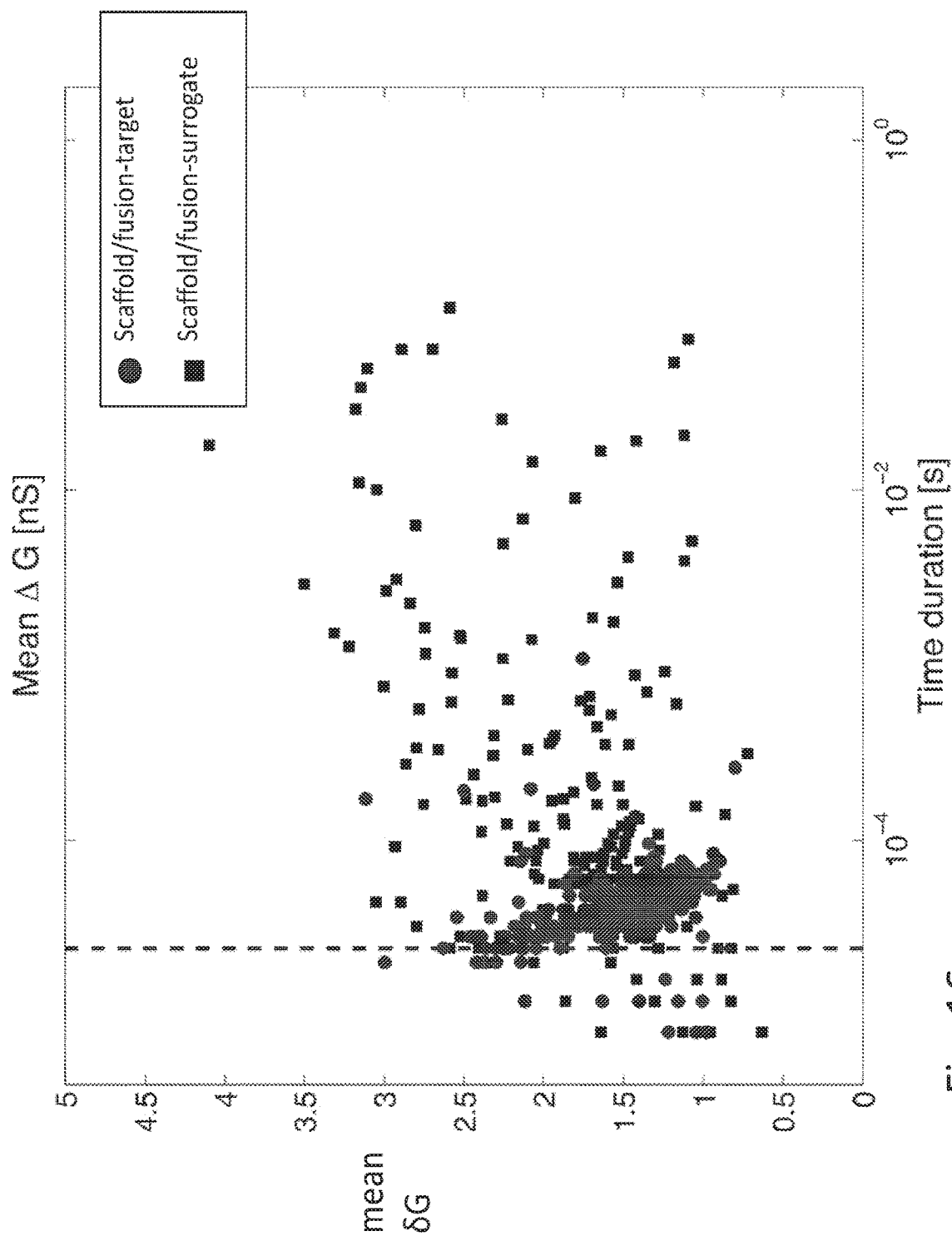
FIG. 16 shows the scatter plot of δG versus duration for all scaffold/fusion-target events and then all scaffold/fusion-surrogate events recorded on the same pore.

Once complex formation was verified, the samples were diluted to the indicated concentration in running buffer (1M LiCl, 10 mM Tris, 1 mM EDTA, pH 8), and the samples were placed into a nanopore device for nanopore analysis (FIG. 16). First, 1074 bp DNA-PNA-NEM at 0.2 nM produced 389 events over 15 minutes (Median, IQR) dwell= (44, 16) μsec, at an event rate of 0.45 sec$^{-1}$ ($R^2$=0.9972). Subsequently, 1074 bp DNA-PNA-PEG at 0.2 nM produce 251 events over 15 minutes, again with an increase in longer events (Median, IQR) dwell=(60, 252) μsec, and at a capture rate of 0.2742 sec$^{-1}$ ($R^2$=0.9972) and for 25% trimmed data.

By applying the framework established in the section "Assigning Statistical Significance to Detection," we assigned statistical confidence to detecting the DNA/PNA-NEM complex as the type 2 molecule and DNA/PNA-PEG as the type 1 molecule. A suitable criterion is to tag an event as type 2 if it is faster than 0.07 ms. The DNA/PNA-PEG can be used as the negative control, to compute the false positive q1=0.554 (55.4%). The DNA/PNA-NEM (type 2) control produced $Q(p) \pm Q_{sd}(p)$=95.3728±2.7436 at 99% confidence. From equation (1) of the mathematical framework, the result is $Q(p) - Q_{sd}(p)$=0.926>0.554, which means we can say that DNA/PNA-NEM molecules are present with 99% confidence.

Figure 17:
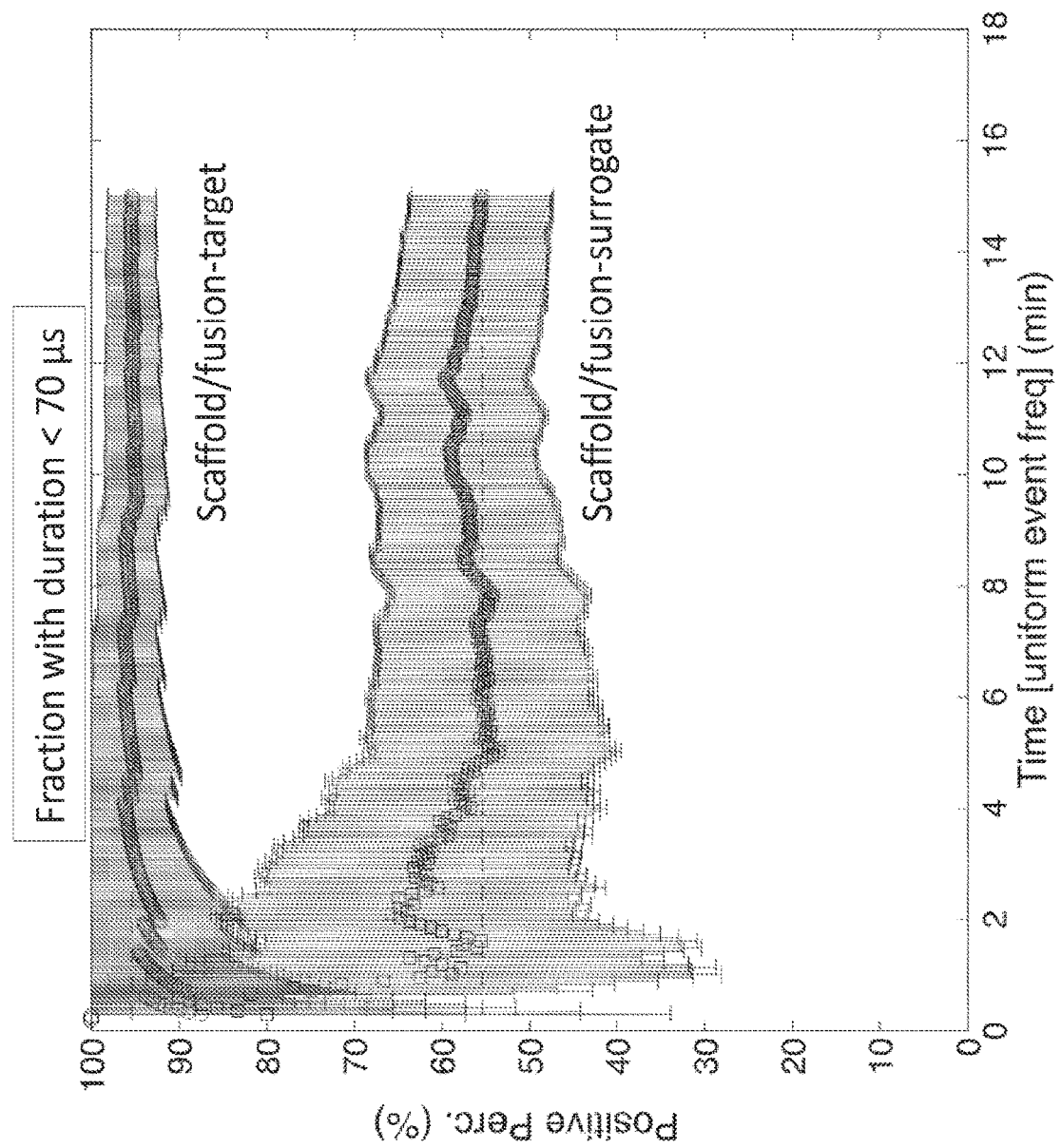
FIG. 17 shows the evolution of the percentage of events with duration below 70 μs, recorded over time, from the populations in FIG. 13. The error bars quantitate the uncertainty in the measured percentage.

A plot of $Q(p) \pm Q_{sd}(p)$ as a function of recording time is shown for each reagent type (DNA/PNA-NEM and DNA/PNA-PEG) in FIG. 17. Observe that DNA/PNA-NEM complexes were detected with 99% confidence within the first minute of recording.

We next varied the PEG:NEM ratios at 50:1, 10:1 and 2:1 to assess how competition for the bisPNA binding sites would be observed in the nanopore device, and in particular when the PEG surrogate was held constant.

Figure 18:
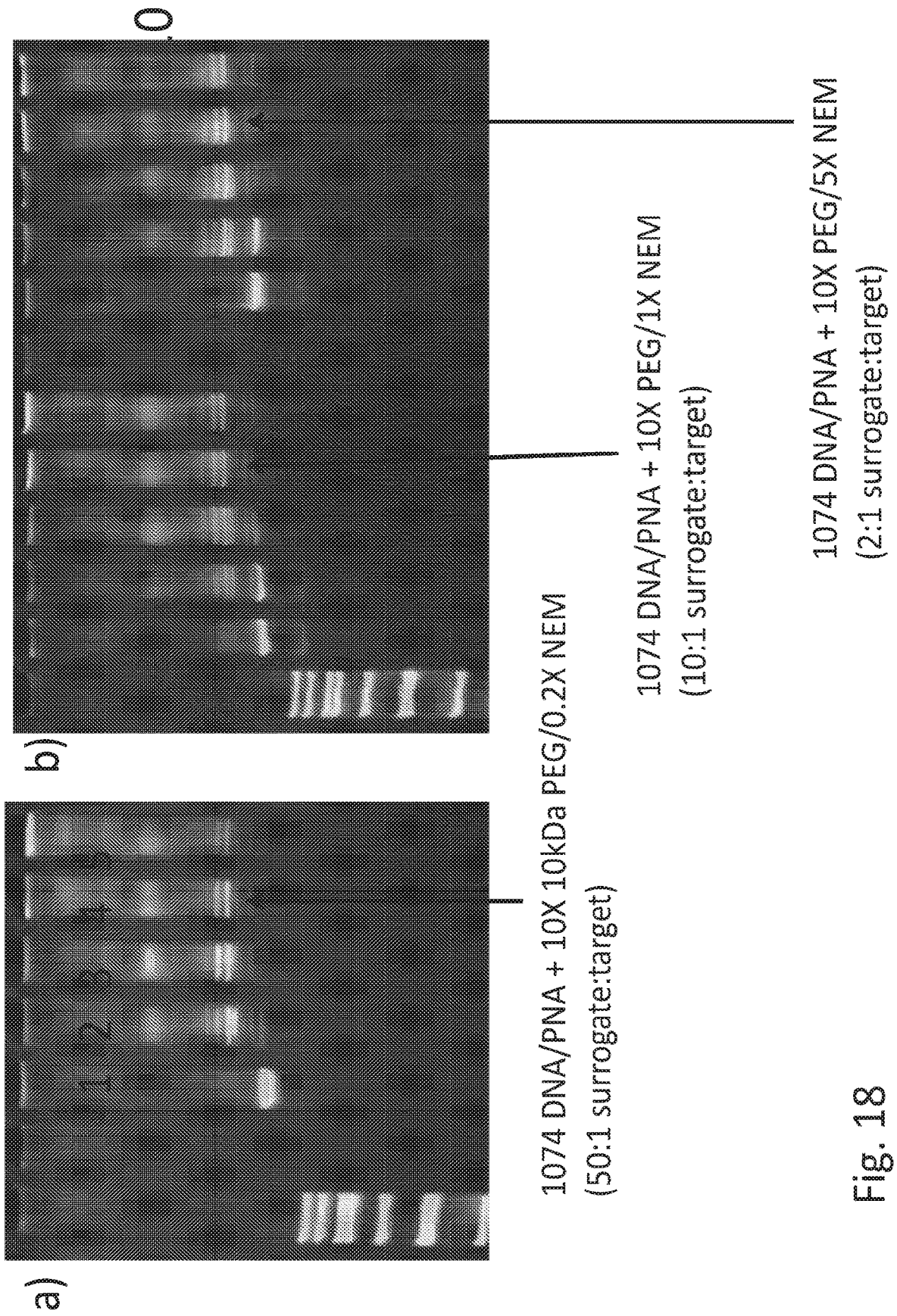
FIG. 18 shows a gel comparing the electrophoretic mobility of the scaffold/fusion-target and scaffold/fusion-surrogate complexes with a surrogate:target competition ratio of 50:1 ((a), lane 4) and 10:1 ((b), lane 4) and 2:1 ((b), lane 9), with all three tested on the nanopore. As before, NEM is the target and PEG is the surrogate, with each competing for a binding site on a PNA that binds to the DNA scaffold.

A 5% polyacrylamide gel (FIG. 18) was run to assess the binding of dsDNA by a solution of PNA molecules tagged with NEM (target) and 10 kDa PEG (surrogate). FIG. 18(a) shows a 10% polyacrylamide gel was ran to assess the DNA binding capacity of PNA that had reacted with a solution containing PEG and NEM at a 50:1 molar ratio. 1074 bp DNA was incubated with increasing amounts of the fully reacted PNA at concentrations spanning 10 to 100-fold molar excess (FIG. 18(a), Lanes 2-5). Nanopore analysis was conducted on the sample exhibiting complete DNA binding by the PNA-PEG and PNA-NEM species (FIG. 18(a), Lane 4). FIG. 18(b) shows a 10% polyacrylamide gel that ran to assess the DNA binding capacity of PNA bound to PEG and increasing amounts of NEM (10:1 and 2:1 PEG to NEM molar ratios respectively). 1074 bp DNA was incubated with increasing amounts of the bound PNA at concentrations spanning 10 to 100-fold molar excess (Lanes 2-5=10:1 ratio, Lanes 7-10=2:1 ratio). Nanopore analysis was conducted on the sample exhibiting complete DNA binding by the PNA-PEG and PNA-NEM species (FIG. 18(b), Lanes 4 and 9).

Figure 19:
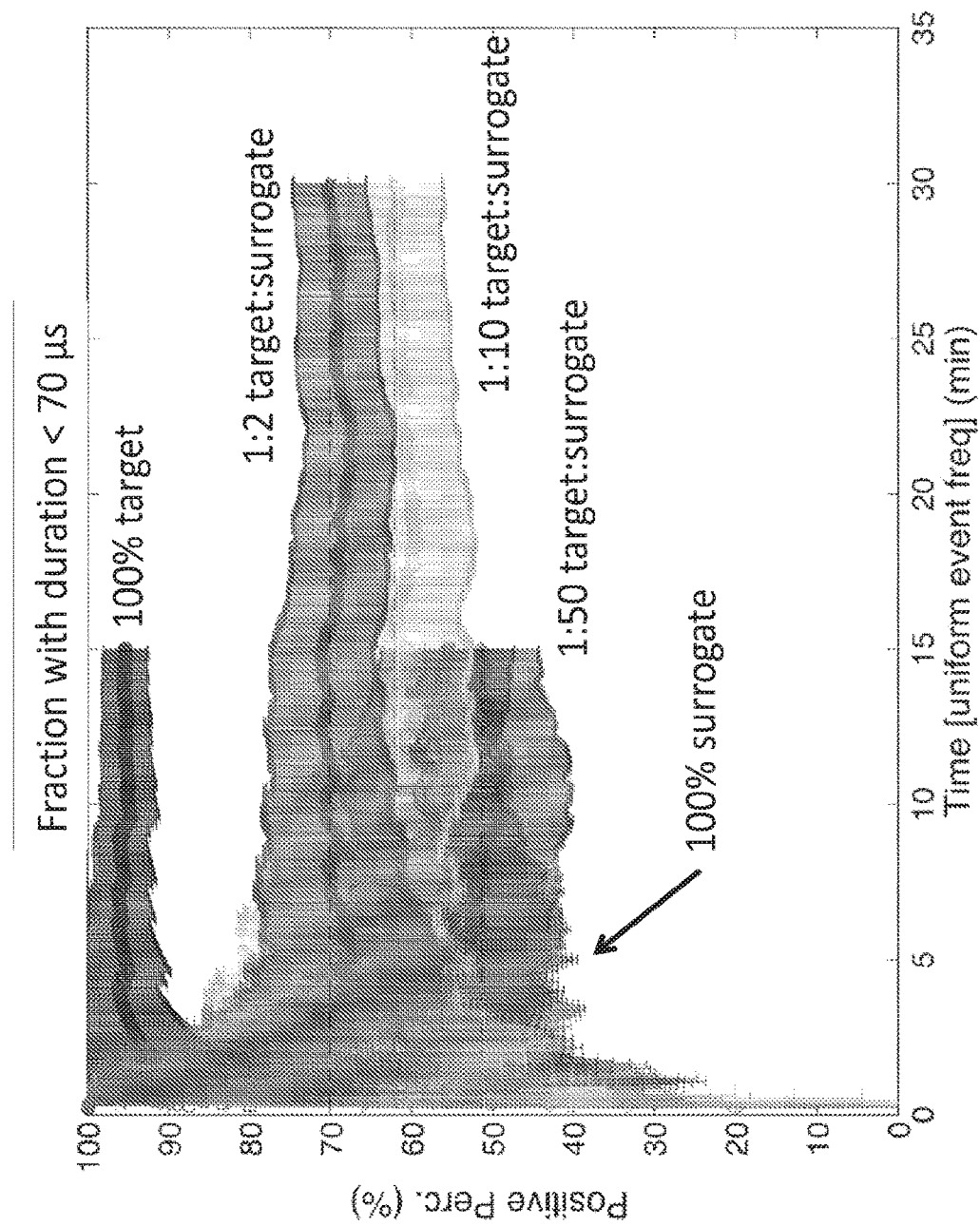
FIG. 19 shows the evolution of the percentage of events with duration below 70 μs, recorded over time, from the populations in FIG. 18. The error bars quantitate the uncertainty in the measured percentage. The fraction of events faster than 70 μs increases as the target:surrogate ratio increases.

First, on the same pore, 1074 bp DNA-PNA-10×PEG and 0.2×NEM (50:1 surrogate:target) produced 337 events over 15 minutes with a population that was indistinguishable from the PEG only assay (Median, IQR) dwell=(68, 210) μsec. The fraction of events faster than 0.07 ms was $Q(p) \pm Q_{sd}(p) = 51.3353 +/- 7.0132$ at 99% confidence, which was not high enough to infer detection of the presence of DNA/PNA-NEM. That is, since equation (1) is not satisfied, we cannot say DNA/PNA-NEM was present in this test with a 50:1 surrogate:target ratio. Subsequently, 1074 bp DNA-PNA-10×PEG and 1×NEM produced 472 events over 30 minutes (Median, IQR) dwell=(60, 76) μsec. The fraction of events faster than 0.07 ms increased to $Q(p) \pm Q_{sd}(p) = 62.0763 +/- 5.7526$ at 99% confidence, as the relative amount of NEM to PEG was increased. From equation (1) of the mathematical framework, the result is $Q(p) - Q_{sd}(p) = 0.563 > 0.554$, which means we can say that DNA/PNA-NEM molecules are present with 99% confidence. Lastly, 1074 bp DNA-PNA-10× PEG and 5×NEM produced 687 events over 30 minutes, (Median, IQR) dwell=(52, 48) μsec. The fraction of events faster than 0.07 ms further increased to $Q(p) \pm Q_{sd}(p) = 70.0146 +/- 4.5029$ at 99% confidence, as the relative amount of NEM to PEG was increased. Again, from equation (1) of the mathematical framework, the result is $Q(p) - Q_{sd}(p) = 0.655 > 0.554$, which means we can say that DNA/PNA-NEM molecules are present with 99% confidence. FIG. 19 shows a plot of $Q(p) \pm Q_{sd}(p)$ as a function of recording time for each reagent type.

As in Example 2, the trend of increasing fraction as the relative amount of NEM to PEG increases shows that competition between NEM and PEG is detectable with the nanopore. Such measurements can be used to detect the presence of the target small molecule, as shown here for NEM and with 99% confidence. Such measurements can also be combined with biophysical models to estimate the target small molecule concentration. $Q(end) = 63.5015 +/- 6.7551$ at 99% confidence

The invention claimed is:

1. A method for detecting the presence or absence of a target molecule suspected to be present in a sample, comprising:
providing a device comprising a layer, wherein said layer separates an interior space of the device into a first volume and a second volume, wherein said layer comprises a nanopore connecting said first volume and said second volume, and wherein the device comprises a sensor configured to identify objects passing through the nanopore;
providing a surrogate molecule, a fusion molecule, and a polymer scaffold, said polymer scaffold covalently bound to said fusion molecule, wherein said fusion molecule comprises a target molecule binding domain adapted to bind to said surrogate molecule or said target molecule;
performing a competition assay by combining said surrogate molecule and said fusion molecule with said sample, wherein said target molecule competes with said surrogate molecule for binding to said target molecule binding domain if said target molecule is present in said sample;
loading said sample into said first volume;
applying a voltage across said nanopore, wherein said first volume comprises said polymer scaffold, said fusion molecule, said surrogate molecule, and said sample suspected of comprising said target molecule, wherein said polymer scaffold is covalently bound to said fusion molecule, and wherein said fusion molecule binds to said surrogate molecule or said target molecule; and
detecting the presence or absence of the target molecule in said sample.

2. The method of claim 1, wherein said voltage induces translocation of said polymer scaffold with the fusion molecule bound to said target molecule or bound to said surrogate molecule from said first volume through said nanopore to generate an electrical signal detected by said sensor.

3. The method of claim 2, wherein said signal comprises changes in said electrical signal as a function of time.

4. The method of claim 3, further comprising analyzing said changes in electrical signal as a function of time to determine the presence or absence of said target molecule in said sample.

5. The method of claim 1, wherein said competition assay is performed after loading said sample into said first volume.

6. The method of claim 1, wherein said competition assay is performed before loading said sample into said first volume.

7. The method of claim 1, wherein the method further comprises binding a payload molecule to the surrogate molecule, wherein the surrogate molecule comprises a payload binding site adapted to bind to the payload molecule.

8. The method of claim 7, wherein said payload molecule is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, and a cholesterol-DNA hybrid.

9. The method of claim 7, wherein said payload molecule comprises an electrical charge.

10. The method of claim 9, wherein said charged payload molecule is selected from the group consisting of: a peptide, an amino acid, a charged nanoparticle, a synthetic molecule, a nucleotide, a polynucleotide, a metal, and an ion.

11. The method of claim 7, wherein said surrogate molecule is bound to said payload molecule via an interaction selected from the group consisting of: a covalent bond, a hydrogen bond, an ionic bond, a van der Waals force, a hydrophobic interaction, a cation-pi interaction, a planar stacking interaction, a metallic bond, and a biotin-avidin interaction.

12. The method of claim 1, wherein said polymer scaffold comprises a negatively or positively charged polymer adapted to translocate through said nanopore from said first volume to said second volume upon application of a voltage potential to said nanopore.

13. The method of claim 1, wherein said polymer scaffold comprises a molecule selected from the group consisting of: deoxyribonucleic acid (DNA), ribonucleic acid (RNA), peptide nucleic acid (PNA), DNA/RNA hybrid, and polypeptide.

14. The method of claim 1, wherein said sensor is an electrical sensor.

15. The method of claim 14, wherein said sensor detects current flow through said nanopore upon application of a voltage across said nanopore.

16. The method of claim 4, wherein said analysis of changes in electrical signal as a function of time comprises segregating events due to translocation of said polymer scaffold with the fusion molecule bound to said surrogate molecule through the nanopore, and events due to translocation of said polymer scaffold with the fusion molecule bound to said target molecule through said nanopore.

17. The method of claim 1, wherein said method provides a confidence of detection of said target molecule of greater than 90%, 95%, 98%, or 99%.

18. A method for quantifying the amount of a target molecule present in a sample, comprising:
providing a device comprising a layer, wherein said layer separates an interior space of the device into a first volume and a second volume, wherein said layer comprises a nanopore connecting said first volume and said second volume, and wherein the device comprises a sensor configured to identify objects passing through the nanopore;
providing a surrogate molecule, a fusion molecule, and a polymer scaffold, said fusion molecule comprising a target molecule binding domain adapted to bind said surrogate molecule or said target molecule;
performing a competition assay by combining said surrogate molecule and said fusion molecule with said sample, wherein said target molecule competes with said surrogate molecule for binding to said target molecule binding domain if said target molecule is present in said sample;
loading said sample into said first volume;
applying a voltage across said nanopore, wherein said first volume comprises said polymer scaffold, said fusion molecule, said surrogate molecule, and said sample suspected of comprising said target molecule, wherein said polymer scaffold is covalently bound to said fusion molecule, and wherein said fusion molecule binds to said surrogate molecule or said target molecule;
comparing the capture rate of said fusion molecules bound to said target molecule in the nanopore with the capture rate of said fusion molecule bound to said surrogate molecule in the nanopore to quantify the amount of target molecule in said sample.

19. A method for detecting the presence or absence of a target molecule suspected to be present in a sample, comprising:
providing a device comprising a layer, wherein said layer separates an interior space of the device into a first volume and a second volume, wherein said layer comprises a nanopore connecting said first volume and said second volume, and wherein the device comprises a sensor configured to identify objects passing through the nanopore;
providing a surrogate molecule, a fusion molecule, and a polymer scaffold, said fusion molecule comprising a target molecule binding domain;
performing a competition assay by combining said surrogate molecule and said fusion molecule with said sample, wherein said target molecule competes with said surrogate molecule for binding to said target molecule binding domain if said target molecule is present in said sample;
forming a scaffold/fusion molecule complex when the fusion molecule binds to said polymer scaffold;
loading said sample into said first volume;
applying a voltage across said nanopore, wherein said first volume comprises said scaffold/fusion molecule complex, and said sample suspected of comprising said target molecule; and
detecting the presence or absence of the target molecule in said sample.

20. The method of claim 19, wherein said voltage induces translocation of said scaffold/fusion molecule complex bound to said target molecule or bound to said surrogate molecule from said first volume through said nanopore to generate an electrical signal detected by said sensor, and wherein the method further comprises analyzing changes in said electrical signal as a function of time to determine the presence or absence of said target molecule in said sample.

21. The method of claim 19, wherein said polymer scaffold of the scaffold/fusion molecule complex comprises a negatively or positively charged polymer adapted to translocate through said nanopore from said first volume to said second volume upon application of a voltage potential to said nanopore, and wherein said surrogate molecule comprises a payload binding site adapted to bind to a payload molecule selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid, a peptide, an amino acid, a charged nanoparticle, a synthetic molecule, a nucleotide, a polynucleotide, a metal, and an ion.

22. A method for detecting the presence or absence of a target molecule suspected to be present in a sample, comprising:
providing a device comprising a layer, wherein said layer separates an interior space of the device into a first volume and a second volume, wherein said layer comprises a nanopore connecting said first volume and said second volume, and wherein the device comprises a sensor configured to identify objects passing through the nanopore;
providing a surrogate molecule and a polymer scaffold, wherein said polymer scaffold is adapted to bind to said surrogate molecule or said target molecule;
performing a competition assay by combining said surrogate molecule with said sample, wherein said target molecule competes with said surrogate molecule for binding to said polymer scaffold if said target molecule is present in said sample;
loading said sample into said first volume;
applying a voltage across said nanopore, wherein said first volume comprises said polymer scaffold, said surrogate molecule, and said sample suspected of comprising said target molecule, wherein said polymer scaffold is bound to said surrogate molecule or said target molecule; and
detecting the presence or absence of the target molecule in said sample.

23. The method of claim 22, wherein said voltage induces translocation of said polymer scaffold bound to said target molecule or bound to said surrogate molecule from said first volume through said nanopore to generate an electrical signal detected by said sensor, and wherein the method further comprises analyzing changes in said electrical signal as a function of time to determine the presence or absence of said target molecule in said sample.

24. The method of claim 22, wherein said polymer scaffold comprises a negatively or positively charged polymer adapted to translocate through said nanopore from said first volume to said second volume upon application of a voltage potential to said nanopore, and wherein said surrogate molecule comprises a payload binding site adapted to bind to a payload molecule selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid, a peptide, an amino acid, a charged nanoparticle, a synthetic molecule, a nucleotide, a polynucleotide, a metal, and an ion.

* * * * *